US007655414B2

(12) United States Patent
Brennscheidt et al.

(10) Patent No.: US 7,655,414 B2
(45) Date of Patent: Feb. 2, 2010

(54) DETERMINATION OF RESPONDERS TO CHEMOTHERAPY

(75) Inventors: Ulrich Brennscheidt, Riehen (CH); Otmar Herrgott, legal representative, Freiburg (DE); Astrid Heller, Penzberg (DE); Verena Lutz, Munich (DE); Joachim Moecks, Mannheim (DE); Carol Ward, Helfrantzkirch (FR)

(73) Assignee: Hoffman La-Roche Inc., Nutley, NJ (US)

( * ) Notice: Subject to any disclaimer, the term of this patent is extended or adjusted under 35 U.S.C. 154(b) by 0 days.

(21) Appl. No.: 11/431,241

(22) Filed: May 10, 2006

(65) Prior Publication Data

US 2007/0054330 A1 Mar. 8, 2007

(30) Foreign Application Priority Data

May 11, 2005 (EP) .................................. 05010244
May 23, 2005 (EP) .................................. 05011070

(51) Int. Cl.
*G01N 33/53* (2006.01)
(52) U.S. Cl. ........................................................ 435/7.1
(58) Field of Classification Search .................... 435/7.1
See application file for complete search history.

(56) References Cited

U.S. PATENT DOCUMENTS

| 4,816,567 | A | 3/1989 | Cabilly et al. |
| 4,943,533 | A | 7/1990 | Mendelsohn et al. |
| 5,212,290 | A | 5/1993 | Vogelstein et al. |
| 5,562,925 | A | 10/1996 | Rosenberg et al. |
| 5,891,996 | A | 4/1999 | Mateo de Acosta del Rio et al. |
| 6,881,555 | B2 | 4/2005 | Guo et al. |
| 2004/0157255 | A1 | 8/2004 | Agus et al. |

FOREIGN PATENT DOCUMENTS

| EP | 0659439 | 6/1995 |
| WO | WO 96/40210 | 12/1996 |
| WO | WO 98/50433 | 11/1998 |
| WO | WO 01/00245 | 1/2001 |
| WO | WO 01/34574 | 5/2001 |
| WO | WO 01/72721 | 10/2001 |
| WO | WO 02/39117 | 5/2002 |
| WO | WO 2004/046386 | 6/2004 |
| WO | WO 2004/063709 | 7/2004 |

OTHER PUBLICATIONS

Ono et al (Molecular Cancer Therapeutics, Apr. 2004, 3(4):465-472.*
Cell Signaling Technology datasheets for antibodies #4058.*
Cell Signaling Technology datasheets for antibodies #9106.*
Huang et al (Cancer Research, Aug. 2004, 64:5355-5362).*
Cappuzzo et al (Journal of the National Cancer Institute, Aug. 2004, 96(15):1133-1141).*
Ono et al (Molecular Cancer Therapeutics, Apr. 2004, 3(4):465-472).*
Hidalgo (Oncology (Williston Park), Nov. 2003, 17(11 Suppl 12):abstract).*
Tockman et al (Cancer Res., 1992, 52:2711s-2718s).*
Gatzemeir, U. et al, *Proc Am Soc Clin Oncol* 23 (2004) 617 (Abstraft 7010).
Herbst, R.S., et al, *J. Clin Oncol* (2004) ASCO Annual Meeting Proceedings Ed: 22 (Jul. 15 Suppl) (Abstract 7011).
Capuzzo, F. et al, *JNCI* 96 (2004) 1133-1141.
Han, S.W. et al, *J Clin Oncol* 23 (2005) 2493-2501.
Mukohara, T. et al, *Lung Cancer* 41 (2003) 123-130.
Raben, D. et al, *Int J Radiation Oncology Biol Phys* 59 (2004) 27-38.
Ono, M. et al, *Mol Cancer Ther* 3 (2004) 465-472.
Hirsch F.R. et al, *Curr Opin Oncol* 17 92005) 118-122.
Janmaat, M. et al., *Clin Cancer Res* 9: (2003) 2316-2326.
Brognard, J. et al, *Cell Death and Differentiation*, 9 (2002) 893-904.
David, O. et al, *Clin. Cancer Res.*, 10 (2004) 6865-6871.
Kakiuchi, S. et al, *Human Molecular Genetics* 13 (2004) 3029-3043.
Kim et al, *Cancer Cell*, 7 (2005) 263-273.
Balsara, B.R. et al, *Carcinogenesis* 25 (2004) 2053-2059.
Hirami, Y. et al, *Cancer Letters*, 214 (2004) 157-164.
Lee, S.H. et al, *AMPIS* 110 (2002) 587-592.
Engelman, J.A. et al, *Proc. Natl. Acad. Sci. USA* 102 (2004) 3788-3793.
David, O., *J. Cell Mol. Med*, 5 (2001) 430-433.
Mantha, A, et al, *Clin. Cancer Res.* 11 (2005) 2398-2407.
Kohler, G. et al, *Nature*, 256 (1975) 495.
Heinemann, V. et al, *Cancer Res*, 48 (1988) 4024.
Staal, S.P. *Proc. Natl. Acad. Sci USA* 84 (1987) 5034-5037.
Nakatani, K. et al, *Biochem. Biophys. Res. Comm* 257 (1999) 906-910.
Dudek H. et al, *Science* 275 (1997) 661-665.
Meier, R., et al, *J. Biol. Chem* 272 (1997) 30491-30497.
Giaccone Giuseppe et al, *J. Clin. Onc.*, 22:5 (2004) 777-784.
Pao William et al, *Proceedings of the Nat'l Acad. of Sci. of the USA*, 101:36 13306-13311 (2004).
Han Sae-Won et al, *Int. J. Cancer*, 113 (2005) 109-115.
Janmaat et al, *Clin. Cancer Res.*, 9 2316-2326 (2003).
Vincent S et al, *Brit. Jour. of Cancer*, 90: 1047-1052 (2004).
Warshamana-Greene G Sakuntala et al, *Clin. Cancer Res: An Offical Jour. of the Amer. Assoc. for Cancer Res.*, 11:4 pp. 1563-1571 (Feb. 2005).

\* cited by examiner

*Primary Examiner*—Sean E Aeder
(74) *Attorney, Agent, or Firm*—George W. Johnston; Dennis P. Tramaloni

(57) ABSTRACT

The present invention relates to a method of determining whether a biological sample comprising human lung cancer cells is sensitive to a combination of an epidermal growth factor receptor inhibitor and a chemotherapeutic agent by determining the overexpression of a phosphorylated AKT protein and/or a phosphorylated MAPK protein in the biological sample. The invention is also related to methods for deriving a candidate agent or for selecting a composition for inhibiting the progression of lung cancer in a patient wherein a phosphorylated AKT protein and/or a phosphorylated MAPK protein is used.

9 Claims, 11 Drawing Sheets

DETERMINATION OF RESPONDERS TO CHEMOTHERAPY

PRIORITY TO RELATED APPLICATIONS

This application claims the benefit of European Application No. 05010244.1, filed May 11, 2005 and European Patent Application No. 05011070.9, filed May 23, 2005, which are hereby incorporated by reference in their entirety.

FIELD OF THE INVENTION

The present invention relates to a method of determining whether a biological sample comprising human lung cancer cells is sensitive to a combination of an epidermal growth factor receptor inhibitor and a chemotherapeutic agent by determining the overexpression of a phosphorylated AKT protein and/or a phosphorylated MAPK protein in the biological sample. The invention is also related to methods for deriving a candidate agent or for selecting a composition for inhibiting the progression of lung cancer in a patient wherein a phosphorylated AKT protein and/or a phosphorylated MAPK protein is used.

BACKGROUND OF THE INVENTION

EGFR, encoded by the erbB1 gene, has been causally implicated in human malignancy. In particular, increased expression of EGFR has been observed in breast, bladder, lung, head, neck and stomach cancer as well as glioblastomas. The Epidermal Growth Factor Receptor (EGFR), a 170-kD glycoprotein, is composed of an N-terminus extracellular domain, a hydrophobic transmembrane domain, and a C-terminus intracellular region containing the kinase domain. EGFR ligand-induced dimerization activates the intrinsic RTK domain (an Src homology domain 1, SH1), resulting in autophosphorylation on six specific EGFR tyrosine residues in the noncatalytic tail of the cytoplasmic domain.

The cellular effects of EGFR activation in a cancer cell include increased proliferation, promotion of cell motility, adhesion, invasion, angiogenesis, and enhanced cell survival by inhibition of apoptosis. Activated EGFR induces tumor cell proliferation through stimulation of the mitogen-activated protein kinase (MAPK) cascade. Upon ligand binding to the EGFR, the SOS guanine nucleotide exchange factor is recruited to the plasma membrane via the Grb2 adaptor protein, which stimulates the exchange of GTP for GDP on the small G-protein Ras, subsequently activating the MAPK cascade consisting of Raf, MEK, and ERK. Activated ERKs (pMAPK, pERK1/2) in turn phosphorylate and activate transcription factors such as ELK-1 or c-Myc, promoting cell growth.

Multiple growth factor pathways contribute to the progression and survival of NSCLC cells through activation of multiple kinases. The EGFR enhances cancer cell survival also by signaling through the phosphatidylinositol-3-kinase (PI3K)/AKT pathway and the STAT pathway. AKT is stimulated also by other growth factors, including insulin growth factor-1, basic fibroblast growth factor, and interleukins 3 and 6. The three isoforms of AKT 1-3 are all phosphorylated (pAKT) in a similar fashion at residues T308 in the activation domain and S473 in the COOH-terminal domain.

Erlotinib (Tarceva® Genentech/OSI) is a potent epidermal growth factor receptor (HER1/EGFR) tyrosine-kinase inhibitor (TKI) that provides survival benefit to patients with non-small-cell lung cancer (NSCLC) who have failed previous chemotherapy when used as a single agent (WO 01/34574). The efficacy of Tarceva® was studied in various trials. Its chemical name is N-(3-ethynylphenyl)-6,7-bis(2-methoxyethoxy) quinazolin-4-amine.

The TALENT trial was a placebo-controlled phase III study in first-line NSCLC patients who received gemcitabine and cisplatin (this concurrent chemoradiotherapy was the non-US standard of care) in combination with erlotinib (Tarceva® at 150 mg/day or placebo with. The primary endpoint was survival duration, with secondary endpoints of time to progression, response rate; duration of response; pharmacokinetic and pharmacodynamic parameters, and quality of life. HER1/EGFR and HER2 expression rates were also assessed. A standard safety analysis was done. The overall outcome of the TALENT trial was negative. For the primary and secondary endpoints there was no demonstrable benefit for erlotinib (Tarceva® plus chemotherapy (gemcitabine and cisplatin) compared with gemcitabine and cisplatin alone (Gatzemeier, U., et al., Proc Am Soc Clin Oncol 23 (2004) 617 (Abstract 7010)). Identical results were seen in the US-based TRIBUTE study, with erlotinib plus carboplatin and paclitaxel (Herbst, R. S., et al., J Clin Oncol (2004) ASCO Annual Meeting Proceedings. Post-Meeting Edition; 22 (July 15 Suppl.) (Abstract 7011)). A randomised, placebo-controlled phase III study of single-agent erlotinib as second- or third-line therapy for non-small-cell lung cancer (NSCLC) (BR.21; NCIC/OSIP) found a statistically significant improvement in survival with erlotinib (6.7 months) compared with placebo (4.7 months).

Various studies are related to the investigation of biomarkers in non-small cell lung cancer and their relation to certain EGFR inhibitor drugs. Han, et al., Int J Cancer 113 (2005) 109-115 investigate 65 patients with Gefitinib (Iressa™, EGFR TKI) monotherapy. They analyse EGFR downstream molecules as response predictive markers for gefitinib in chemotherapy-resistant non-small cell lung cancer. Cappuzzo, F. et al., JNCI 96 (2004) 1133-1141 investigate 106 patients with Gefitinib (Iressa; EGFR TKI) monotherapy. They investigate AKT phosphorylation and gefitinib efficacy in patients with advanced non-small-cell lung cancer and find that patients with P-AKT-positive tumors who received gefitinib benefited more from the therapy that patients with P-AKT-negative tumors. Vicent, S. et al., Br J Cancer 90 (2004) 1047-1052 investigate 111 NSCLC patients. They find that pERK is activated in non-small-cell lung cancer and associated with advanced tumors. Han, S. W. et al., J Clin Oncol 23 (2005) 2493-2501 investigate 90 patients with Gefitinib (EGFR TKI) monotherapy. They analyse the predictive and prognostic impact of Epidermal Growth Factor Receptor Mutation in Non-Small-Cell lung cancer patients treated with gefitinib. Mukohara, T. et al., Lung Cancer 41 (2003) 123-130 investigate 60 patients, 20 patients per stage who either underwent neoadjuvant chemotherapy or radiation. The EGFR expression correlates with pERK and pAKT expression. The sample size is too low as mentioned by the authors themselves. Raben, D. et al., Int J Radiation Oncology Biol. Phys 59 (2004) 27-38 investigate targeted therapies for non-small-cell lung cancer. Ono, M. et al., Mol Cancer Ther 3 (2004) 465-472 assay 9 NSCLC cell lines and treated with gefitinib. Hirsch, F. R. et al., Curr Opin Oncol 17 (2005) 118-122 review the phosphorylation status of AKT and MAPK as potential marker for gefitinib resistance. Meert, et al., Clinical Cancer Research 9 (2003) 2316-2326 investigate NSCLC cell lines in aspect of EGFR inhibitor activity. Neither EGFR nor Her2 expression levels correlate with sensitivity to EGFR inhibitors. Brognard, J. et al., Cell Death and Differentiation 9 (2002) 893-904 analysed 19 NSCLC cell lines were analysed whereby 17 exhibited phosphorylation of Erk1/2 and constitutive activity. David, O. et al., Clinical Cancer Research 10 (2004) 6865-6871 disclose that overexpression of pAKT is an independent prognostic factor in NSCLC. Kakiuchi, S. et al., Human Molecular Genetics 13 (2004) 3029-3043 investigate a genome wide cDNA microarray of 33 NSCLC patients. All were given gefitinib in a monotherapeutical setting. No evidence was found for correlation between AKT/pAKT expression level, EGFR gene status or pEGFR staining and gefitinib response. Kim, R. H. et al., Cancer Cell 7 (2005) 263-273 disclosed that DJ-1 expression, an oncogene, equals pAKT level. Balsara, B. R. et al., Carcinogenesis 25 (2004) 2053-2059 investigate 110 NSCLC patients with TMA pAKT expression. No significant difference in survival exists between pAKT negativity and positivity. Hirami, Y. et al., Cancer Letters 214 (2004) 157-164 investigate the relation of epidermal growth factor receptor, pAKT and hypoxia-inducible factor-1 alpha in non-small cell lung cancers. Lee, S. H. et al., APMIS 110 (2002) 587-592 analyses 43 LN metastasis of NSCLC patients. AKT activation in NSCLC plays a role in tumor development rather than progression. Engelman, J. A. et al., Proc. Natl. Acad. Sci. USA 102 (2004) 3788-3793 analyse erbB-3 mediates phosphoinositide 3-kinase activity in gefitinib-sensitive non-small cell lung cancer cell lines. David, O., J Cell Mol Med 5 (2001) 430-433 discussess the role of AKT and PTEN as new diagnostics markers in lung cancer. Mantha, A. et al., Clin. Cancer Res. 11 (2005) 2398-2407 investigate the targeting of the mevalonate pathway which inhibits the function of the epidermal growth factor receptor.

Prognostic markers associated with EGFR positive cancer are investigated in WO 2004/046386. Gene expression markers for response to EGFR inhibitor drugs are disclosed by US 2004/0157255. Biomarkers and methods for determining sensitivity to epidermal growth factor receptor modulators are disclosed in WO 2004/063709. WO 01/00245 describes humanized anti-ErbB2 antibodies and methods for treating cancer with anti-ErbB2 antibodies, such as humanized anti-erbB2 antibodies.

However, and as suggested by the above cited art, there is still a need to provide methods for determining the sensitivity to EGFR inhibitor therapy, in particular combination therapies of an EGFR inhibitor with a chemotherapeutic agent.

SUMMARY OF THE INVENTION

Accordingly, in one embodiment of the invention, a method is provided of determining whether a biological sample comprising human lung cancer cells is sensitive to a combination of an epidermal growth factor receptor inhibitor and a chemotherapeutic agent, the method comprising determining the overexpression of a phosphorylated AKT protein and/or a phosphorylated MAPK protein in the biological sample whereby the overexpression of the phosphorylated AKT protein and/or the phosphorylated MAPK protein is an indication that the biological sample comprising human lung cancer cells is sensitive to a combination of a epidermal growth factor receptor inhibitor and a chemotherapeutic agent.

In another embodiment of the invention, an antibody that binds to the phosphorylated AKT protein or an antibody that binds to the phosphorylated MAPK protein is used for determining whether a biological sample comprising human lung cancer cells is sensitive to a combination of a epidermal growth factor inhibitor and a chemotherapeutic agent.

In another embodiment of the invention, a method of selecting a composition for inhibiting the progression of lung cancer in a patient is provided, the method comprising: separately exposing aliquots of a biological sample comprising lung cancer cells that are sensitive to a combination of an EGFR inhibitor and a chemotherapeutic agent from the patient in the presence of a plurality of test compositions;

comparing the level of expression of a phosphorylated AKT protein and/or a phosphorylated MAPK protein in the aliquots of the biological sample contacted with the test compositions and the level of expression of the phosphorylated AKT protein and/or the phosphorylated MAPK protein in an aliquot of the biological sample not contacted with the test compositions, selecting one of the test compositions which alters the level of expression of the marker genes in the aliquot containing that test composition, relative to the aliquot not contacted with the test composition wherein an at least 10% difference between the level of expression of the phosphorylated AKT protein and/or the phosphorylated MAPK protein in the aliquot of the biological sample contacted with the test composition and the level of expression of the phosphorylated AKT protein and/or the phosphorylated MAPK protein in the aliquot of the biological sample not contacted with the test composition is an indication for the selection of the test composition.

In yet another embodiment of the invention, a method of deriving a candidate agent is provided, said method comprising:

a) contacting an aliquot of a biological sample containing lung cancer cells that are sensitive to an EGFR inhibitor and a chemotherapeutic agent with the candidate agent, b) determining the level of expression of a phosphorylated AKT protein and/or a phosphorylated MAPK protein in the aliquot of the biological sample contacted with the candidate agent and determining the level of expression of the phosphorylated AKT protein and/or the phosphorylated MAPK protein in an aliquot of the biological sample not contacted with the candidate agent, c) observing the effect of the candidate agent by comparing the level of expression of the phosphorylated AKT protein and/or the phosphorylated MAPK protein in the aliquot of the biological sample contacted with the candidate agent and the level of expression of the phosphorylated AKT protein and/or the phosphorylated MAPK protein in the aliquot of the biological sample not contacted with the candidate agent, d) deriving said agent from said observed effect, wherein an at least 10% difference between the level of expression of the phosphorylated AKT protein and/or the phosphorylated MAPK protein in the aliquot of the biological sample contacted with the candidate agent and the level of expression of the phosphorylated AKT protein and/or the phosphorylated MAPK protein in the aliquot of the biological sample not contacted with the candidate agent is an indication of an effect of the candidate agent.

In another embodiment of the invention, a candidate agent derived by the method according to the invention is provided and a pharmaceutical preparation comprising an agent according the invention.

In still another embodiment of the invention an agent according to the invention is used for the preparation of a composition for the inhibition of progression of lung cancer.

In yet another embodiment of the invention, a method of producing a drug comprising the steps of the method of the invention and (i) synthesizing the candidate agent identified in step (c) or an analog or derivative thereof in an amount sufficient to provide said drug in a therapeutically effective amount to a subject; and/or (ii) combining the drug candidate the candidate agent identified in step (c) or an analog or derivative thereof with a pharmaceutically acceptable carrier.

In still another embodiment of the invention, a kit comprising an antibody against phosphorylated MAPK and/or phosphorylated AKT protein is provided.

DESCRIPTION OF THE FIGURES

FIG. 1

Figure 1:
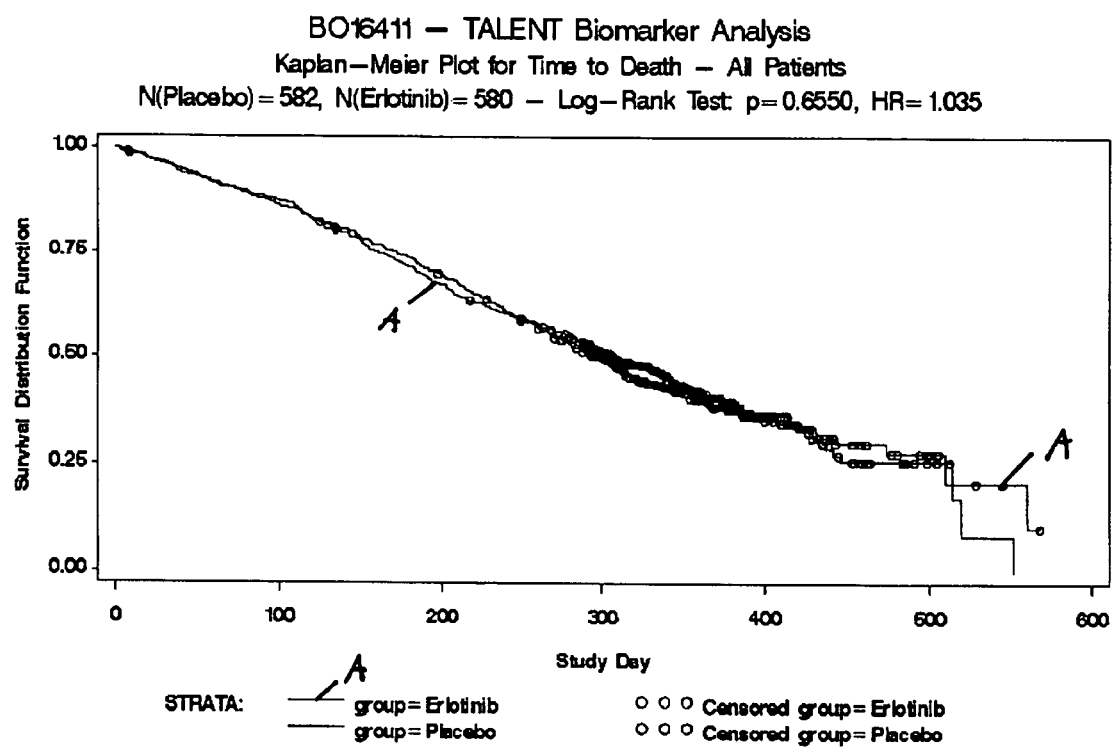
FIGS. 1-11 Kaplan-Meier plots of the results of example 1.
Figure 2:
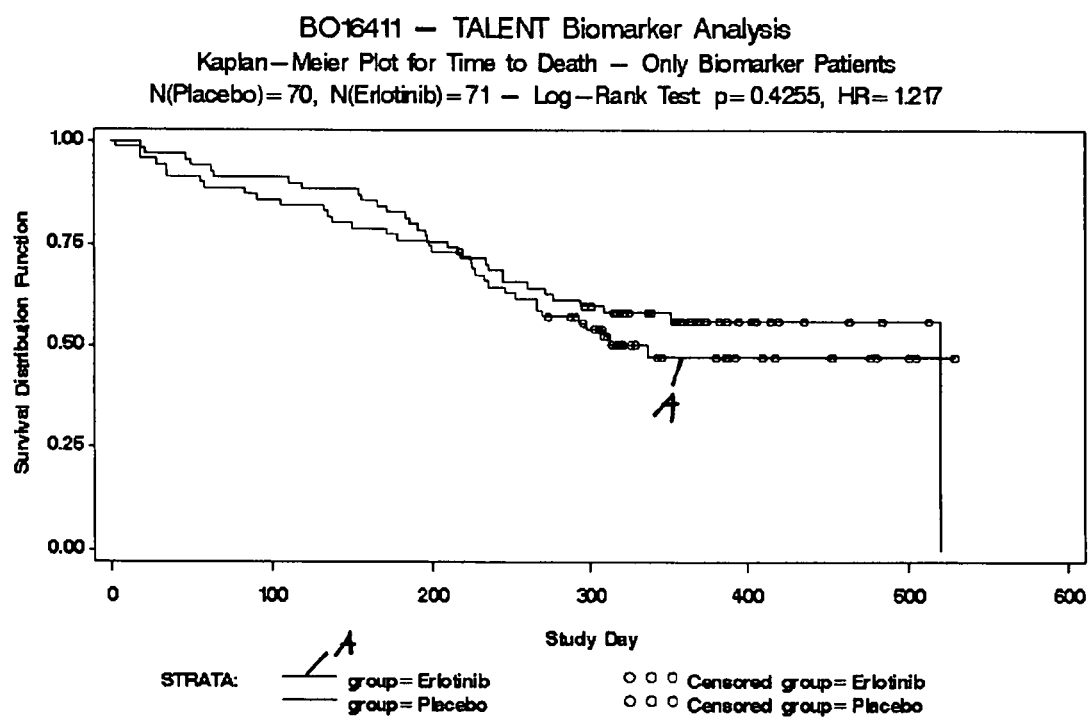
Figure 3:
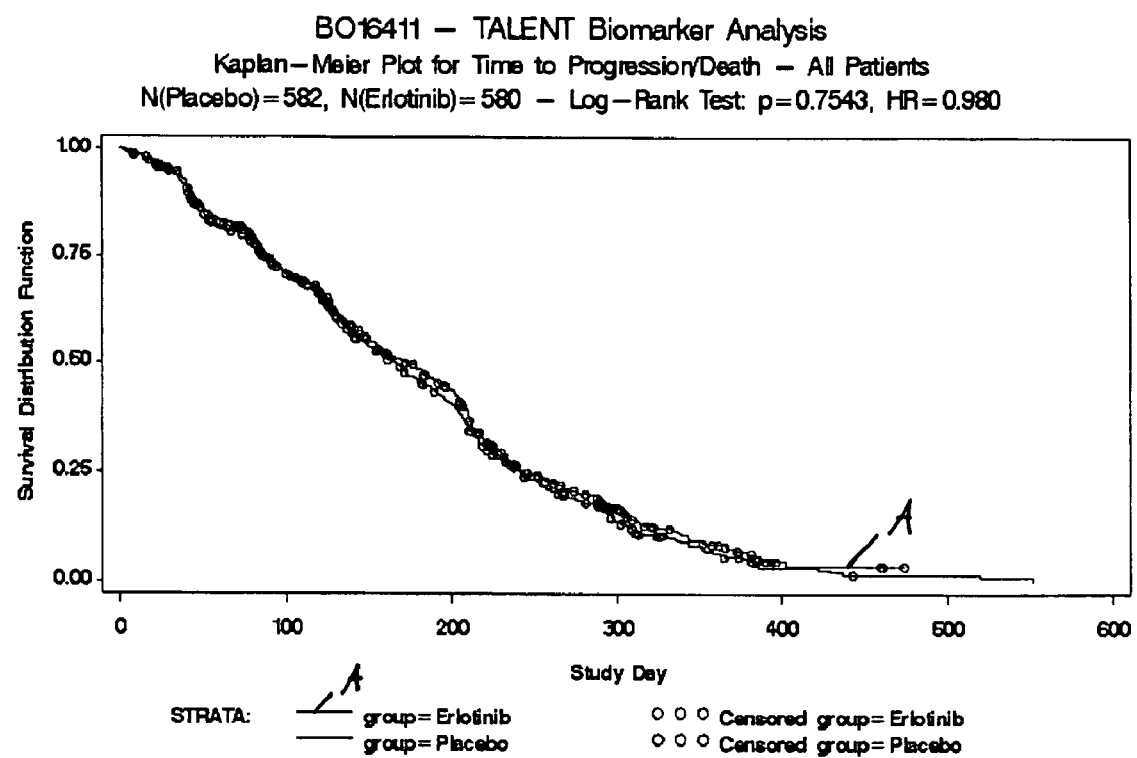
Figure 4:
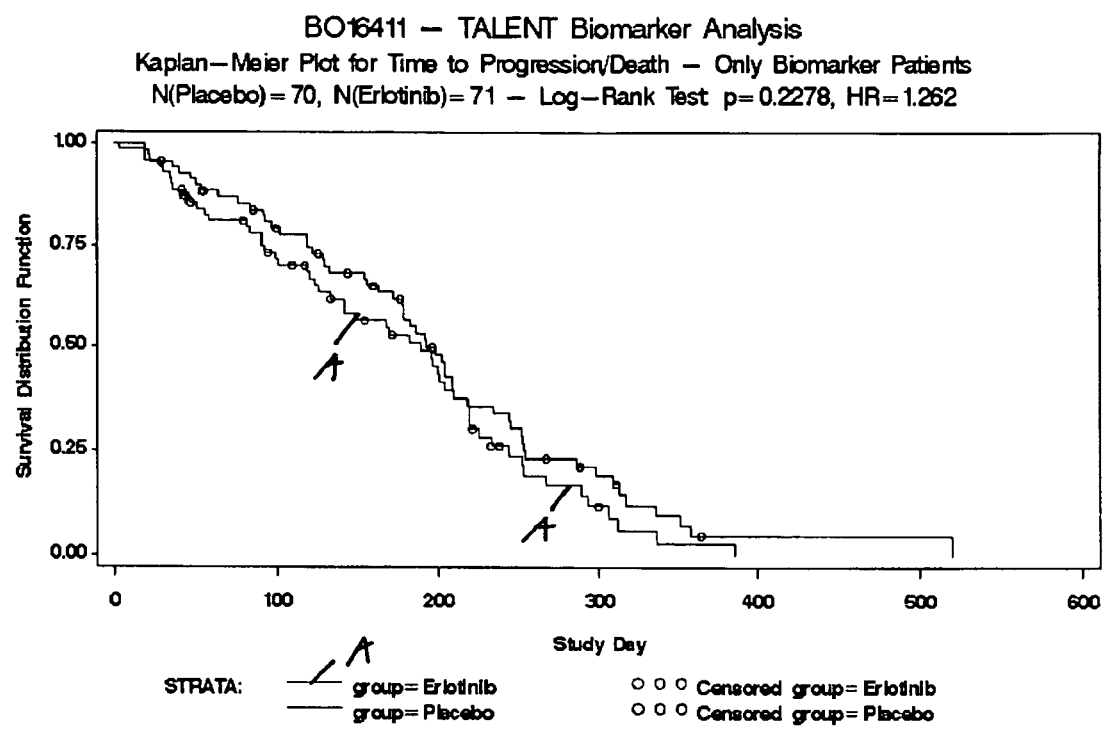
Figure 5:
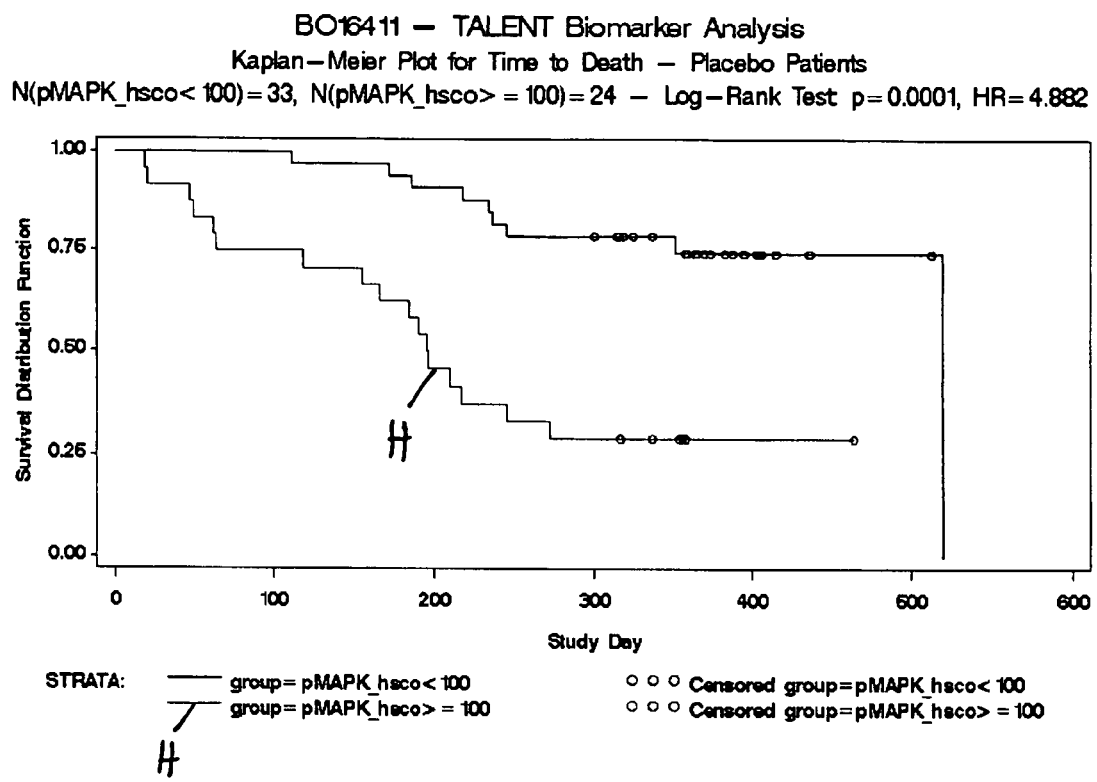
Figure 6:
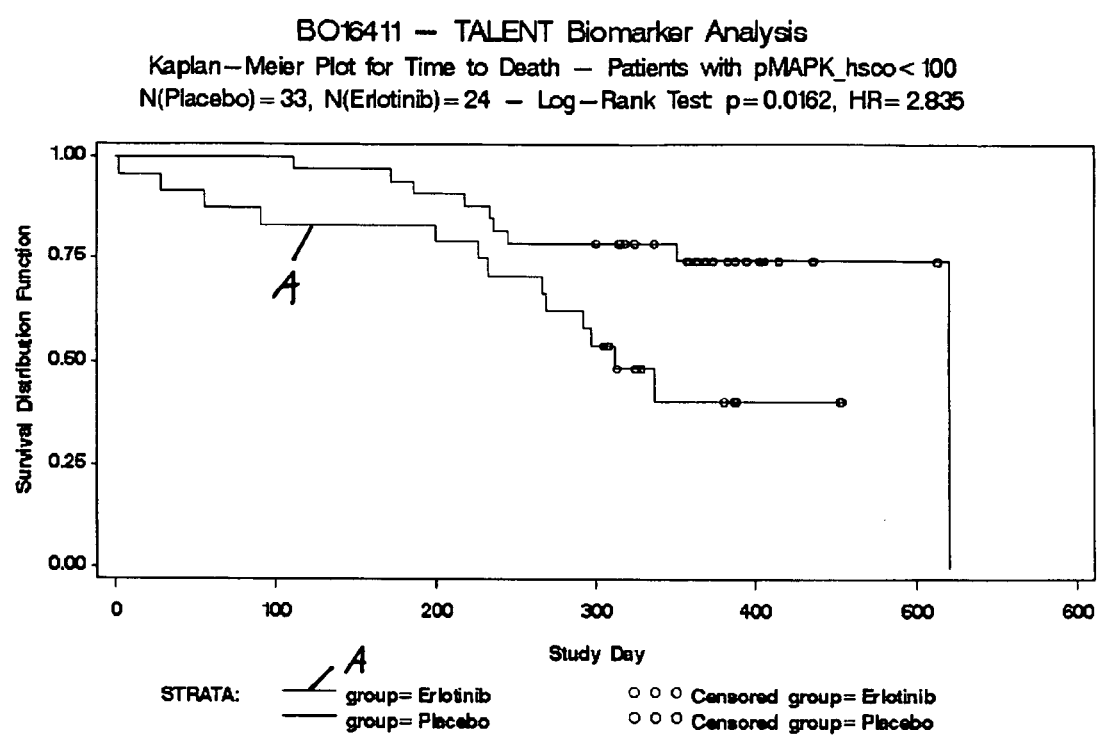
Figure 7:
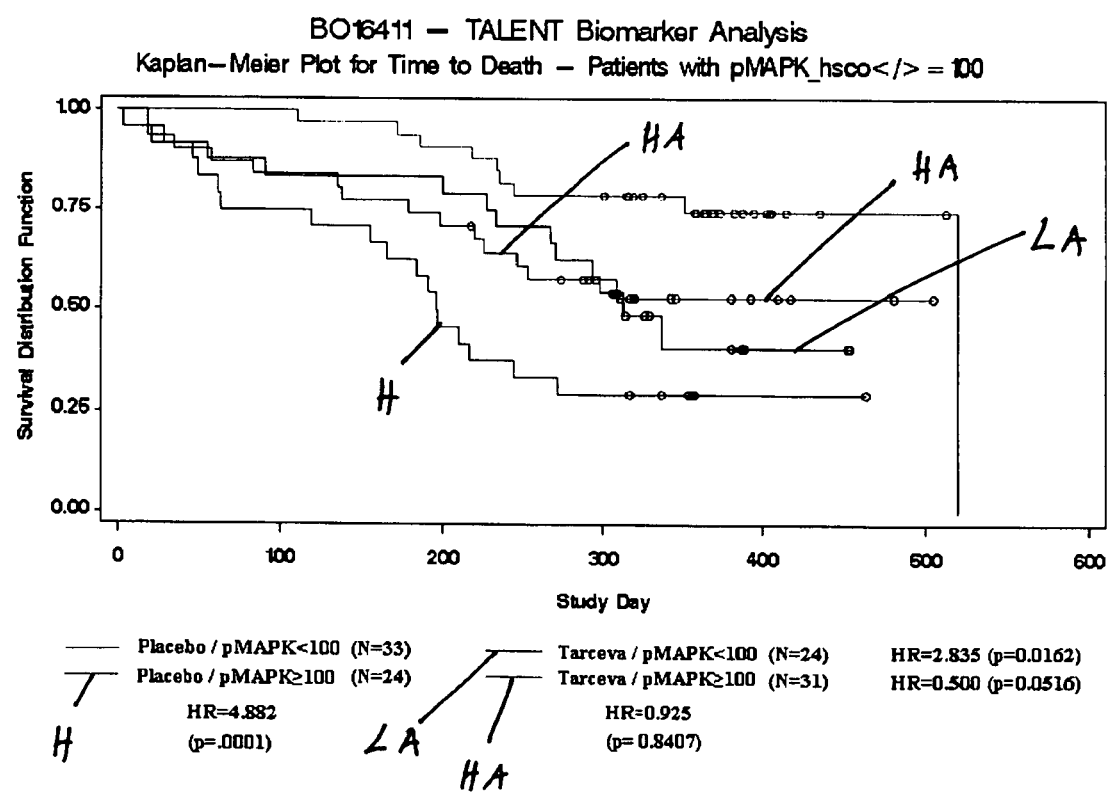
Figure 8:
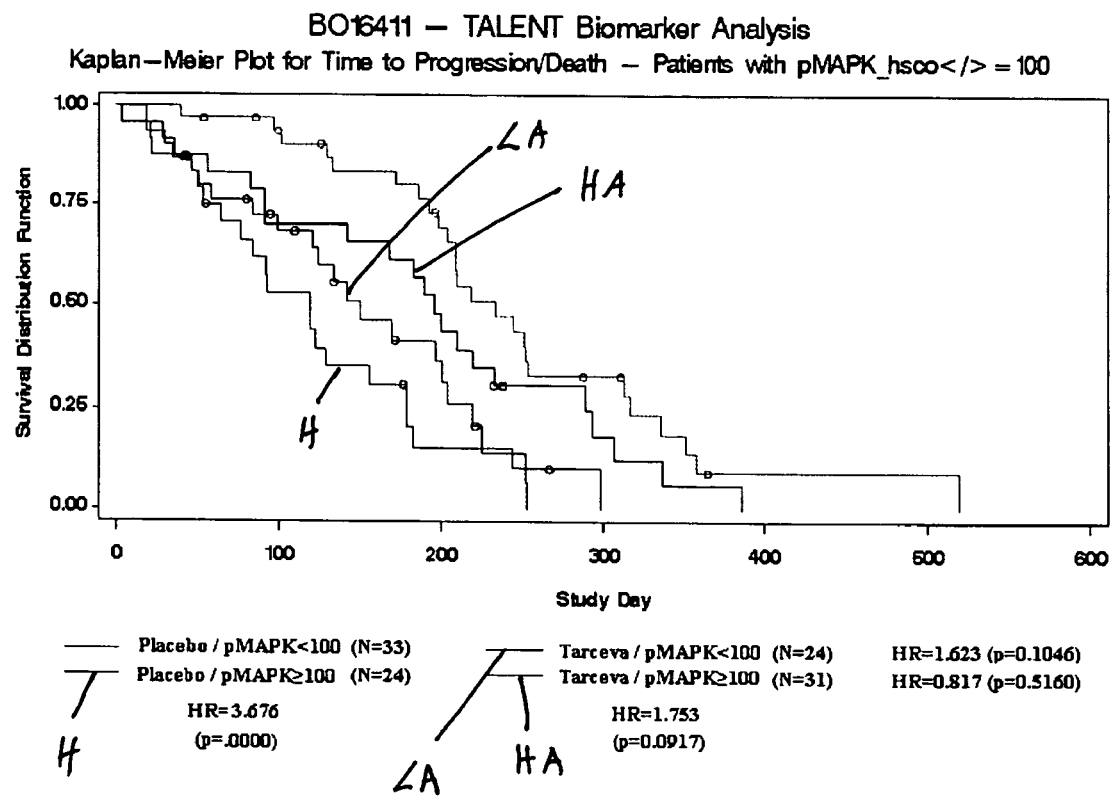

Kaplan-Meier curves for time to death (OS) analysis among all patients randomly assigned to Erlotinib/Gemcitabine/Cisplatin (A) or Placebo/Gemcitabine/Cisplatin treatment (circles indicate censored observation times, when the observation was terminated before the event occurred)

FIG. 2

Kaplan-Meier curves for time to death (OS) analysis among all patients with biomarker data, randomly assigned to Erlotinib/Gemcitabine/Cisplatin (A) or Placebo/Gemcitabine/Cisplatin treatment (circles indicate censored observation times, when the observation was terminated before the event occurred)

FIG. 3

Kaplan-Meier curves for time to progression/death (PFS) analysis among all patients randomly assigned to Erlotinib/Gemcitabine/Cisplatin (A) or Placebo/Gemcitabine/Cisplatin treatment (circles indicate censored observation times, when the observation was terminated before the event occurred)

FIG. 4

Kaplan-Meier curves for time to progression/death (PFS) analysis among all patients with biomarker data, randomly assigned to Erlotinib/Gemcitabine/Cisplatin (A) or Placebo/Gemcitabine/Cisplatin treatment (circles indicate censored observation times, when the observation was terminated before the event occurred)

FIG. 5

Kaplan-Meier curves for time to death (OS) analysis among all biomarker patients treated with Placebo/Gemcitabine/Cisplatin comparing patients with pMAPK H-Score ☐100 (H) with patients with pMAPK H-Score<100 (circles indicate censored observation times, when the observation was terminated before the event occurred)

FIG. 6

Kaplan-Meier curves for time to death (OS) analysis among all biomarker patients with pMAPK H-Score<100 comparing Erlotinib/Gemcitabine/Cisplatin (A) with Placebo/Gemcitabine/Cisplatin treatment (circles indicate censored observation time, when the observation was terminated before the event occurred)

FIG. 7

Kaplan-Meier curves for time to death (OS) analysis among all biomarker patients with pMAPK H-Score<100 and pMAPK H-Score ☐100 comparing Erlotinib/Gemcitabine/Cisplatin (LA, HA) with Placebo/Gemcitabine/Cisplatin (H) treatment, respectively (circles indicate censored observation times, when the observation was terminated before the event occurred)

FIG. 8

Kaplan-Meier curves for time to progression/death (PFS) analysis among all biomarker patients with pMAPK H-Score<100 and pMAPK H-Score ☐100 comparing Erlotinib/Gemcitabine/Cisplatin (LA, HA) with Placebo/Gemcitabine/Cisplatin (H) treatment, respectively (circles indicate censored observation times, when the observation was terminated before the event occurred)

FIG. 9

Kaplan-Meier curves for time to death (OS) analysis among all Placebo/Gemcitabine/Cisplatin treated biomarker patients comparing pAKT1 H-Score<300 (L) and pAKT1 H-Score ☐300 (H) (circles indicate censored observation times, when the observation was terminated before the event occurred)

FIG. 10

Kaplan-Meier curves for time to death (OS) analysis among all Erlotinib/Gemcitabine/Cisplatin treated biomarker patients comparing pAKT1 H-Score<300 (L) and pAKT1 H-Score ☐300 (H) (circles indicate censored observation times, when the observation was terminated before the event occurred)

FIG. 11

Kaplan-Meier curves for time to death (OS) analysis among all biomarker patients with pAKT1 H-Score<300 and pAKT1 H-Score ☐300 comparing Erlotinib/Gemcitabine/Cisplatin (LA, HA) with Placebo/Gemcitabine/Cisplatin (H) treatment, respectively (circles indicate censored observation times, when the observation was terminated before the event occurred)

DETAILED DESCRIPTION

Definitions

The term "biological sample" shall generally mean any sample obtained from an individual, body fluid, cell line, tissue culture, or other biological source. Body fluids are e.g. lymph, sera, plasma, urine, semen, synovial fluid and spinal fluid. According to the invention, the biological sample comprises lung cancer cells and non-lung cancer cells (other cells). Methods for obtaining tissue biopsies and body fluids from mammals are well known in the art.

The term "level of expression" or "expression level" generally refers to the amount of an amino acid product or protein in the sample, preferably the amount of a phosphorylated amino acid product or phosphorylated protein in the sample according to the invention. "Expression" refers to the process by which a gene coded information is converted into the structures present and operating in the cell including their phosphorylation according to the invention. As used herein, "expressed genes" include those that are transcribed into mRNA and then translated into protein and post translationally modified e.g. phosphorylated. Just for the sake of completeness, this term shall also include the expressed genes that are transcribed into RNA but not translated into a protein (for example, transfer and ribosomal RNAs). The terms "overexpression" and "underexpression" refer to an upward or a downward deviation respectively in levels of expression as compared to the baseline expression level in a sample used as a control. "Overexpression" is therefore also "increased expression" and "underexpression" is "decreased expression".

The term "antibody" herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be constructed as requiring production of the antibody by any particular method. For example, the monoclonal antibodies to be used in accordance with the present invention may be made by the hybridoma method first described by Kohler, G. et al., Nature 256 (1975) 495, or may be made by recombinant DNA methods (see, e.g., U.S. Pat. No. 4,816,567). "Antibody fragments" comprise a portion of an intact antibody.

An antibody "which binds" an antigen of interest according to the invention, i.e., the phosphorylated MAPK or the phosphorylated pAKT protein, is one capable of binding that antigen with sufficient affinity such that the antibody is useful in detecting the presence of the antigen. The antibody according to the invention is one which binds phosphorylated MAPK or phosphorylated pAKT protein, it will usually preferentially bind phosphorylated MAPK or phosphorylated pAKT protein as opposed to the non-phosphorylated MAPK or the non-phosphorylated pAKT protein or does not significantly cross-react with non-phosphorylated MAPK or non-phosphorylated pAKT protein. In such embodiments, the extent of binding of the antibody to the non-phosphorylated proteins will be less than 10% as determined by fluorescence activated cell sorting (FACS) analysis or radioimmunoprecipitation (RIA). In other words, it will specifically bind phosphorylated MAPK or phosphorylated pAKT protein and does not specifically bind or does not all bind non-phosphorylated MAPK or non-phosphorylated pAKT protein.

A "chemotherapeutic agent" is a chemical compound useful in the treatment of cancer. Examples of chemotherapeutic agents include alkylating agents such as thiotepa and cyclosphosphamide (CYTOXAN™), alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as adacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, poffiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL®, Bristol-Myers Squibb Oncology, Princeton, N.J.) and docetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition, are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. The "chemotherapeutic agent" itself can be a combination of chemical compounds useful in the treatment of cancer combination as mentioned above, i.e. the combination may be gemcitabine/cis-platin, but also e.g. cis-platin/paclitaxel, cis-platin/docetaxel, cis-platin/vinorelbine, gemcitabine/carboplatin, or carboplatin/docetaxel.

The term "EGFR inhibitor" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); antibodies that bind type 11 mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO 98/50433, Abgenix). The anti-EGFR antibody may be conjugated with a cytotoxic agent, thus generating an immunoconjugate (see, e.g., EP 0 659 439 A2, Merck Patent GmbH). Examples of small molecules that bind to EGFR include ZD1839 or Gefitinib (IRESSA™; Astra Zeneca), CP-358774 or Erlotimils (Tarceva®; Genentech/OSI) and AG1478, AG1571 (SU 5271; Sugen). Particularly preferred in this application are EGFR tyrosine kinase inhibitors, particularly small molecule EGFR tyrosine kinase inhibitors as e.g. erlotinils (Tarceva®). A "small molecule" can be e.g. a peptide or a peptidomimetics with a molecular weight less than about 10,000 grams per mole, preferably less than about 5,000 grams per mole. Preferably, a "small molecule" is compound, i.e. an organic or inorganic compound, with a molecular weight less than about 5,000 grams per mole, preferably less than about 1,000 grams per mole, more preferably less than 500 grams per mole, and salts, esters, and other pharmaceutically acceptable forms of such compounds. Therefore, in a preferred embodiment of the invention, the EGFR inhibitor is a EGFR tyrosine kinase inhibitor that is a compound with a molecular weight less than about 5,000 grams per mole, preferably less than about 1,000 grams per mole, and salts, esters, and other pharmaceutically acceptable forms of such a compound. In other words, the EGFR inhibitor is a compound that inhibits EGFR tyrosine kinase activity and that has a molecular weight less than about 5,000 grams per mole, preferably less than about 1,000 grams per mole, more preferably less than 500 grams per mole, and salts, esters, and other pharmaceutically acceptable forms of such a compound.

"Gemcitabine" is the chemotherapeutic agent 2',2'-difluorodeoxycytidine (dFdC) which is a pyrimidine analogue of deoxycytidine in which the deoxyribose moiety contains two fluorine atoms at the 2'-position (see Heinemann, V. et al., Cancer Res 48 (1988) 4024). It is commerciably available as Gemzar® from Eli Lilly and Company, Indianapolis, Ind., USA.

"Cis-platin" as used throughout this application is the chemotherapeutic agent cis-diamminedichloroplatinum (see U.S. Pat. No. 5,562,925) commercially available as Platinol® from Bristol-Myers Squibb Company, New York, N.Y., USA. "Cis-platin" is a heavy metal complex containing a central atom of platinum surrounded by two chloride atoms and two ammonia molecules in the cis position.

According to the invention, the expression that "a biological sample comprising human lung cancer cells is sensitive to a combination of an epidermal growth factor receptor inhibitor and a chemotherapeutic agent" shall mean that the biological sample comprising human lung cancer cells is sensitive to a treatment with a combination of an epidermal growth factor receptor inhibitor and a chemotherapeutic agent in contrast to a treatment with an epidermal growth factor receptor inhibitor alone. "Sensitive" can also be understood as "reacting to" or "showing a reaction to", particularly such a reaction that is of benefit to a lung cancer patient. Thereby, it can be determined whether a lung cancer patient is sensitive to to a treatment with a combination of an epidermal growth factor receptor inhibitor and a chemotherapeutic agent in contrast to a treatment with an epidermal growth factor receptor inhibitor alone. This means that the patient will benefit from such a treatment.

A "MAPK" protein is a member of a highly conserved cytosolic serine/threonine protein kinase family known as mitogen-activated protein kinases (MAPKs) or extracellular signal-regulated kinases (ERKs). This protein family has several subgroups. ERKs are activated and tyrosine- or threonine-phosphorylated in response to a wide variety of extracellular signals, including osmotic stress, heat shock, proinflammatory cytokines, hormones, and mitogens. The term "MAPK protein" as used in this invention preferably refers to a member of the MAPK protein family comprising or preferably consisting of MAPK1 and MAPK3. The amino acid sequences of MAPK1 (ERK2) are SEQ ID NO: 1) and MAPK3 (ERK1) (SEQ ID NO: 2). These amino amino acid sequences are encoded by the mRNA sequences, i.e. cDNA sequences SEQ ID NO: 3 and 4 for MAPK1 ans SEQ ID NO: 5 for MAPK3. The primary phosphorylation sites in MAPK1 are Thr185 and Tyr185 and the primary phosphorylation in MAPK3 are Thr202 and Tyr204. These phosphorylation sites are also recognized by the antibody used in the present invention, i.e. preferably the polyclonal antibody serum against the phosphorylated forms of MAPK1 and MAPK3.

The term "AKT" protein refers to a protein of the AKT/PKB subfamily of second-messenger regulated serine/threonine protein kinases which has three members termed AKT1/PKBalpha, AKT2/PKBbeta (Staal, S. P., Proc. Natl. Acad. Sci. USA 84 (1987) 5034-5037) and AKT3/PKBgamma (Nakatani, K. et al., Biochem. Biophys. Res. Comm. 257 (1999) 906-910; U.S. Pat. No. 6,881,555) respectively. The isoforms are homologous and are activated by phosphorylation in response to phosphatidylinositol 3'-OH kinase (PI3K) signaling. The PI3K/AKT/PKB pathway appears to be important for regulating cell survival/cell death (Dudek, H. et al., Science 275 (1997) 661-665) also in tumorigenesis. The term "AKT protein" as used in this invention preferably refers to a member of the AKT protein family comprising or preferably consisting of AKT1, AKT2 and AKT3. Phosphorylation of AKT1/PKBα occurs on two sites $Thr^{308}$ and on $Ser^{473}$ (Meier, R., et al., J. Biol. Chem. 272 (1997) 30491-30497). Equivalent phosphorylation sites occur in AKT2/PKBbeta ($Thr^{309}$ and $Ser^{474}$) and AKT3/PKBgamma ($Thr^{305}$ and $Ser^{472}$). The term "phosphorylated AKT" protein refers to a phosphorylated "AKT" protein, preferably phosphorylated at the sites described above. The term "MAPK protein" as used in this invention preferably refers to a member of the MAPK protein family comprising or preferably consisting of MAPK1 and MAPK3. AKT 1 is also known as human RAC-alpha serine/threonine-protein kinase (EC 2.7.1.37) (RAC-PK-alpha), Protein kinase B (PKB) (C-AKT) and the amino acid sequence of AKT 1 is SEQ ID NO: 6. AKT2 is also known as human RAC-beta serine/threonine-protein kinase (EC 2.7.1.37) (RAC-PK-beta), Protein kinase AKT-2 or Protein kinase B, beta (PKB beta) and the amino acid sequence of AKT 2 is SEQ ID NO: 7. AKT3 is also known as human RAC-gamma serine/threonine-protein kinase (EC 2.7.1.37) (RAC-PK-gamma), protein kinase AKT-3 or Protein kinase B, gamma (PKB gamma) (STK-2) and the amino acid sequence of AKT 3 is SEQ ID NO: 8.

Conventional techniques of molecular biology and nucleic acid chemistry, which are within the skill of the art, are explained in the literature. See, for example, Sambrook, J. et al., Molecular Cloning: A Laboratory Manual, Cold Spring Harbor Laboratory Press, Cold Spring Harbor, N.Y., 1989; Gait, M. J. (ed.), Oligonucleotide Synthesis—A Practical Approach, IRL Press, 1984; Hames, B. D., and Higgins, S. J. (eds.), Nucleic Acid Hybridisation—A Practical Approach, IRL Press, 1985; and a series, Methods in Enzymology, Academic Press, Inc., all of which are incorporated herein by reference. All patents, patent applications, and publications mentioned herein, both supra and infra, are incorporated herein by reference.

DETAILED DESCRIPTION OF THE INVENTION

In one embodiment of the invention, a method is provided of determining whether a biological sample comprising human lung cancer cells is sensitive to a combination of an epidermal growth factor receptor inhibitor and a chemotherapeutic agent, the method comprising determining the overexpression of a phosphorylated AKT protein and/or a phosphorylated MAPK protein in the biological sample whereby the overexpression of the phosphorylated AKT protein and/or the phosphorylated MAPK protein is an indication that the biological sample, comprising human lung cancer cells is sensitive to a combination of a epidermal growth factor receptor inhibitor and a chemotherapeutic agent.

Preferably, in the method according to the invention, the overexpression of phosphorylated AKT protein and/or phosphorylated MAPK protein in the biological sample is determined by
a) determining the level of expression of phosphorylated AKT protein and/or phosphorylated MAPK protein in the biological sample,
b) determining the level of expression of phosphorylated AKT protein and/or phosphorylated MAPK protein in a biological sample comprising human lung cancer cells that are not sensitive a combination of a epidermal growth factor inhibitor and a chemotherapeutic agent,
c) determining the difference of the level of expression of phosphorylated AKT protein and/or phosphorylated MAPK protein determined in step a) and b) thereby determining the overexpression of phosphorylated AKT protein and/or phosphorylated MAPK protein.

Preferably, the difference of the level of expression of phosphorylated AKT protein and/or phosphorylated MAPK protein determined in step a) and b) is at least 10%. More preferably, the difference of the level of expression of phosphorylated AKT protein and/or phosphorylated MAPK protein determined in step a) and b) is at least 25%. In another embodiment, the difference of the level of expression of phosphorylated AKT protein and/or phosphorylated MAPK protein determined in step a) and b) is at least 50%, 75%, 100%, 125%, 150%, 175%, 200%, 300%, 400%, 500% or 1,000%. The difference of the level of expression of phosphorylated AKT protein and/or phosphorylated MAPK protein determined in step a) and b) can be up to 10,000 or 50,000%. The difference of the level of expression of phosphorylated AKT protein and/or phosphorylated MAPK protein determined in step a) and b) is preferably between 10% to 10,000%, more preferably 25% to 10,000%, 50% to 10,000%, 100% to 10,000%, even more preferably 25% to 5,000%, 50% to 5,000%, 100% to 5,000%.

In a preferred embodiment of the invention, the biological sample is a primary lung tumor or a metastasis (regional or distant) which can be obtained e.g. by lung biopsy or from other organs by way of biopsy. A metastasis can also be a distant metastasis e.g. from the liver or lymph node. It has to be noted that such distant metastasis also contain lung cancer cells as the metastases originate from the lung.

In another preferred embodiment the cancer is another cancer than lung cancer as pancreatic cancer. However, other cancers with solid tumours are also feasible such as ovarian, colorectal, head and neck, renal cell carcinoma, glioma and gastrointestinal cancers, particularly stomach cancer.

In another preferred embodiment the EGFR inhibitor is a EGFR tyrosine kinase inhibitors, particularly small molecule EGFR tyrosine kinase inhibitors as e.g. Tarceva®. Therefore in other words, in a particularly preferred embodiment of the invention, the EGFR inhibitor is erlotinib or N-(3-ethynylphenyl)-6,7-bis(2-methoxyethoxy)quinazolin-4-amine.

In yet another preferred embodiment of the invention, the chemotherapeutic agent(s) is selected from the group consisting of gemcitabine and/or cis-platin.

In another preferred embodiment of the invention, the overexpression of the phosphorylated AKT protein or of the phosphorylated MAPK protein is determined using a reagent (such as for example an antibody) which specifically binds the phosphorylated protein and preferably not specifically or not at all to the non-phosphorylated protein. Preferably the reagent is an antibody, an antibody derivative, or an antibody fragment which specifically binds to the phosphorylated AKT protein or the phosphorylated MAPK protein and preferably not specifically or not at all to the non-phosphorylated AKT protein or the non-phosphorylated MAPK protein.

In yet another preferred embodiment of the invention, the phosphorylated AKT protein is phosphorylated at an amino acid position corresponding to amino acid position 473 of the AKT1 protein or the MAPK protein is phosphorylated at amino acid positions corresponding to amino acid positions 202 and 204 of MAPK1. Preferably, the amino acid sequence of the MAPK protein is selected from the group consisting of the amino acid sequence SEQ ID NO: 1 or 2 and the amino acid sequence of the AKT protein is selected from the group consisting of the amino acid sequence SEQ ID NO: 6, 7 or 8.

There are many different types of immunoassays which may be used in the method of the present invention, e.g. enzyme linked immunoabsorbent assay (ELISA), fluorescent immunosorbent assay (FIA), chemical linked immunosorbent assay (CLIA), radioimmuno assay (RIA), and immunoblotting. For a review of the different immunoassays which may be used, see: Lottspeich and Zorbas (eds.), Bioanalytik, $1^{st}$ edition 1998, Spektrum Akademischer Verlag, Heidelberg, Berlin, Germany. Therefore, in yet another preferred embodiment of the invention, the expression level is determined using a method selected from the group consisting of proteomics, flow cytometry, immunocytochemistry, immunohistochemistry and enzyme-linked immunosorbent assay.

In a preferred embodiment of the invention, the overexpression of phosphorylated AKT protein and/or phosphorylated MAPK protein is determined by
a) immunohistochemically staining the biological sample,
b) assigning a grade selected from the numbers 1, 2, 3 and 4 for the level of expression of the phosphorylated AKT protein and/or the phosphorylated MAPK protein upon visual inspection of the staining of the cells in the biological sample whereby the highest detectable grade for the level of expression is assigned,
c) determining the percentage of cells with the highest detectable grade in the immunohistochemically stained biological sample,
d) multiplying the assigned grade with the percentage of cells with the highest detectable grade in the immunohistochemically stained biological sample and with the number 100, and
e) determining overexpression of phosphorylated AKT protein and/or phosphorylated MAPK protein in the biological sample when the result of the multiplication in step d) is above 100.

In another embodiment of the invention, a method is provided of determining whether a lung cancer patient benefits from a combination of an epidermal growth factor receptor inhibitor and a chemotherapeutic agent, the method comprising determining the overexpression of a phosphorylated AKT protein and/or a phosphorylated MAPK protein in a sample from the patient whereby the overexpression of the phosphorylated AKT protein and/or the phosphorylated MAPK protein is an indication that the patient benefits from a combination of a epidermal growth factor receptor inhibitor and a chemotherapeutic agent. All other preferred embodiments described above equally apply to this embodiment. Preferably, in the method according to the invention, the overexpression of phosphorylated AKT protein and/or phosphorylated MAPK protein in the sample from the patient is determined by
a) determining the level of expression of phosphorylated AKT protein and/or phosphorylated MAPK protein in the sample from the patient,
b) determining the level of expression of phosphorylated AKT protein and/or phosphorylated MAPK protein in a sample from a lung cancer patient who does not benefit from a combination of a epidermal growth factor inhibitor and a chemotherapeutic agent, c) determining the difference of the level of expression of phosphorylated AKT protein and/or phosphorylated MAPK protein determined in step a) and b) thereby determining the overexpression of phosphorylated AKT protein and/or phosphorylated MAPK protein. The term "benefit" means that the patient does not have a benefit from a treatment with combination of an epidermal growth factor receptor inhibitor and a chemotherapeutic agent in contrast to a treatment with an epidermal growth factor receptor inhibitor alone.

In another preferred embodiment of the invention, an antibody that binds to the phosphorylated AKT protein or an antibody that binds to the phosphorylated MAPK protein is used for determining whether a biological sample comprising human lung cancer cells is sensitive to a combination of a epidermal growth factor inhibitor and a chemotherapeutic agent.

In still another embodiment of the invention, a method of selecting a composition for inhibiting the progression of lung cancer in a patient is provided, the method comprising:

a) separately exposing aliquots of a biological sample comprising lung cancer cells that are sensitive to a combination of an EGFR inhibitor and a chemotherapeutic agent from the patient in the presence of a plurality of test compositions;

b) comparing the level of expression of a phosphorylated AKT protein and/or a phosphorylated MAPK protein in the aliquots of the biological sample contacted with the test compositions and the level of expression of the phosphorylated AKT protein and/or the phosphorylated MAPK protein in an aliquot of the biological sample not contacted with the test compositions, c) selecting one of the test compositions which alters the level of expression of the phosphorylated AKT protein and/or phosphorylated MAPK protein (marker genes) in the aliquot containing that test composition, relative to the aliquot not contacted with the test composition wherein an at least 10% difference between the level of expression of the phosphorylated AKT protein and/or the phosphorylated MAPK protein in the aliquot of the biological sample contacted with the test composition and the level of expression of the phosphorylated AKT protein and/or the phosphorylated MAPK protein in the aliquot of the biological sample not contacted with the test composition is an indication for the selection of the test composition.

Preferably, the difference of the level of expression of phosphorylated AKT protein and/or phosphorylated MAPK protein in step c) is at least 25%. More preferably, the difference of the level of expression of phosphorylated AKT protein and/or phosphorylated MAPK protein in step c) is at least 50%. In another embodiment, the difference of the level of expression of phosphorylated AKT protein and/or phosphorylated MAPK protein in step c) is at least 75%, 100%, 125%, 150%, 175%, 200%, 300%, 400%, 500% or 1,000%. The difference of the level of expression of phosphorylated AKT protein and/or phosphorylated MAPK protein determined in step c) can be up to 10,000 or 50,000%. The difference of the level of expression of phosphorylated AKT protein and/or phosphorylated MAPK protein determined in step c) is preferably between 10% to 10,000%, more preferably 25% to 10,000%, 50% to 10,000%, 100% to 10,000%, even more preferably 25% to 5,000%, 50% to 5,000%, 100% to 5,000%.

In yet another embodiment of the invention, a method of deriving a candidate agent is provided, said method comprising:

a) contacting an aliquot of a biological sample containing lung cancer cells that are sensitive to an EGFR inhibitor and a chemotherapeutic agent with the candidate agent, b) determining the level of expression of a phosphorylated AKT protein and/or a phosphorylated MAPK protein in the aliquot of the biological sample contacted with the candidate agent and determining the level of expression of the phosphorylated AKT protein and/or the phosphorylated MAPK protein in an aliquot of the biological sample not contacted with the candidate agent, c) observing the effect of the candidate agent by comparing the level of expression of the phosphorylated AKT protein and/or the phosphorylated MAPK protein in the aliquot of the biological sample contacted with the candidate agent and the level of expression of the phosphorylated AKT protein and/or the phosphorylated MAPK protein in the aliquot of the biological sample not contacted with the candidate agent, d) deriving said agent from said observed effect, wherein an at least 10% difference between the level of expression of the phosphorylated AKT protein and/or the phosphorylated MAPK protein in the aliquot of the biological sample contacted with the candidate agent and the level of expression of the phosphorylated AKT protein and/or the phosphorylated MAPK protein in the aliquot of the biological sample not contacted with the candidate agent is an indication of an effect of the candidate agent.

Preferably, the difference of the level of expression of phosphorylated AKT protein and/or phosphorylated MAPK protein in step d) is at least 25%. More preferably, the difference of the level of expression of phosphorylated AKT protein and/or phosphorylated MAPK protein in step d) is at least 50%. In another embodiment, the difference of the level of expression of phosphorylated AKT protein and/or phosphorylated MAPK protein in step d) is at least 75%, 100%, 125%, 150%, 175%, 200%, 300%, 400%, 500% or 1,000%. The difference of the level of expression of phosphorylated AKT protein and/or phosphorylated MAPK protein determined in step d) can be up to 10,000 or 50,000%. The difference of the level of expression of phosphorylated AKT protein and/or phosphorylated MAPK protein determined in step d) is preferably between 10% to 10,000%, more preferably 25% to 10,000%, 50% to 10,000%, 100% to 10,000%, even more preferably 25% to 5,000%, 50% to 5,000%, 100% to 5,000%.

In a preferred embodiment said candidate agent is a candidate inhibitory agent or a candidate enhancing agent.

In another embodiment of the invention a candidate agent derived by the method according to the invention is provided.

In yet another embodiment a pharmaceutical preparation comprising an agent according to the invention is provided.

In still another embodiment an agent according to the invention is used for the preparation of a composition for the inhibition of progression of lung cancer.

In yet another embodiment of the invention, a method of producing a drug comprising the steps of the method of the invention is provided and (i) synthesizing the candidate agent identified in step (c) or an analog or derivative thereof in an amount sufficient to provide said drug in a therapeutically effective amount to a subject; and/or (ii) combining the drug candidate the candidate agent identified in step (c) or an analog or derivative thereof with a pharmaceutically acceptable carrier.

In still another embodiment an AKT protein, a MAPK protein, a phosphorylated AKT protein, a phosphorylated MAPK protein, an antibody selectively binding to a phosphorylated AKT protein or a phosphorylated MAPK protein is used for deriving a candidate agent or for selecting a composition for inhibiting the progression of lung cancer in a patient.

In another embodiment of the invention, a kit is contemplated comprising an antibody against phosphorylated MAPK and/or phosphorylated AKT protein. Such kits known in the art further comprise plastics ware which can be used during the amplification procedure as e.g. microtitre plates in the 96 or 384 well format or just ordinary reaction tubes manufactured e.g. by Eppendorf, Hamburg, Germany and all other reagents for carrying out the method according to the invention, preferably an immunoassay, e.g. enzyme linked immunoabsorbent assay (ELISA), fluorescent immunosorbent assay (FIA), chemical linked immunosorbent assay (CLIA), radioimmuno assay (RIA), and immunoblotting. For a review of the different immunoassays and reagents which may be used, see: Lottspeich and Zorbas (eds.), Bioanalytik, $1^{st}$ edition 1998, Spektrum Akademischer Verlag, Heidelberg, Berlin, Germany.

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

Biomarker Analysis on Tumor Tissue Samples

The objective of the exploratory tumor biomarker analyses for the clinical study was the identification of those markers or combinations of markers which predict best for positive or negative clinical outcome of Tarceva® treatment. As the clinical results of the study did not allow to generate hypotheses about how to select patient populations that derive more benefit from the treatment with Tarceva®, special emphasis was on the identification of markers that discriminate between patients (subgroups) that specifically benefit in the Tarceva® combination vs. the chemotherapy-alone control arm. Additionally, the identification of markers that discriminate between patients (subgroup) that have a detrimental effect from the specific combination with Tarceva® vs. the chemotherapy-alone control arm was investigated.

The aim of this study was to analyze tumor-specific biomarker related to the EGFR signaling pathway e.g. EGFR, HER2, pAKT, and pMAPK.

Biomarker data was correlated with clinical data (overall and therapy-specific analysis).

Material and Methods

Clinical Samples:

Biomarker analyses were performed on a sample subset of 141 patients, for which formalin-fixed paraffin embedded (FFPE) tissue blocks from initial diagnosis had been received.

Antibodies for IHC Testing:

| Antibody | Target protein | Slide pretreatment | Dilution |
|---|---|---|---|
| Abcam ab8932 (available from Abcam, Cambridge, United Kingdom) | pAKT (antibody against phosphorylated Ser 473 of AKT) | pressure cooker 120° C./5 min, citrate buffer pH9 | 1:450 |
| Zymed 36-8800 (available from Zytomed GmbH, Berlin, Germany or Invitrogen, Carlsbad, CA, USA) | pMAPK (ERK1 + 2 Thr202/Tyr204) | pressure cooker 120° C./5 min, citrate buffer pH6 | 1:150 | pMAPK IHC Protocol:
1. Cut about 3-4 um thick sections from the Paraffin-Array-blocks.
2. Mount sections on glass slides and let them dry over night.
3. Deparaffinize the slides in xylene followed by descending ethanol series:
   xylene over night
   xylene 2×10 minutes
   abs.Ethanol 2×10 min.
   96% Ethanol 2×5 min.
   80% Ethanol 1×5 min.
   70% Ethanol 2×5 min.
   PBS Buffer 10 min. (change buffer once or twice)
4. Antigene retrival/sample pretreatment Pressure cooker 5 minutes at 120° C. in 1×citrate buffer pH 6 (Biocyc GmbH, order number 400300692). Wash in TBS/PBS (1:10) buffer for 5 minutes
5. Peroxidase Blocking
   Slides are incubated in 3% $H_2O_2$ for 10 minutes.
   Wash 2×5 minutes in TBS/PBS buffer.
6. Antibody Incubation
   Put the slides in normal serum (1.5%) diluted in Tris-Buffer or a other blocking solution.
   Put the primary antibody (Zymed Rabbit anti phospho-ERK1+2 cat no. 36-8800) diluted 1:150 on the slides and incubate it in a humified chamber at 30° C. for 2 hours.
   Wash 2×5 minutes in TBS/PBS buffer.
   Put Envision Polymer HRP (Dako) on the slides and incubate in a humified chamber at 30° C. for 30 minutes.
   Wash 2×5 minutes in TBS/PBS buffer.
7. Detection
   Wash the slides with 0.05 M Tris buffer pH 7.6 for 20 minutes
   Cover slides for 5 minutes with DAB-Chromogen (Liquid DAB Dako code no. K3467) and incubate it for 5-10 minutes.
   Wash the slides with demin. water for 5 minutes to stop the color reaction.
   Counterstain with hematoxyline (Harris Hämatoxylin HTX 31000, Medite GmbH)
   Rinse with water
   Differentiate in HCL-Ethanol
   "blue" for 5 min in water
   Ascending ethanol series
   xylene
   cover pAKT IHC Protocol:

Protocol as for pMAPK, Except
   Compare 4.: Sample pretreatment in citrate buffer pH 9 (Dako code no. S2367)

Compare 6.: Primary antibody (abcam AKT phospho S473) diluted 1:450 (compare 6.)

IHC data Reporting:

One pathologist evaluated all immunostainings. The nuclear staining intensity (pAKT, pMAPK) was estimated by visual inspection in a four step scale (0, 1, 2, 3). In addition to nuclear staining intensity, the percentage of positive cells, and the reason for analysis failure (i.e. lack of tumor cells in the tissue spot or lack of the tissue spot on the TMA slide) was recorded.

Exploratory Statistical Analysis:

The statistical analyses of the biomarker data aimed at exploring the potential to predict clinical benefit and/or toxicities, by each marker separately and/or by suitable combinations.

According to experience many biomarkers show a skewed statistical distribution across patients and within patient. Frequently there is also some biochemical background of this skewness, in that the variation process has a multiplicative structure. Skewed distributions present with problems when linear statistical approaches (e.g. regression) are to be used. When used as covariates in statistical models the skewness as well can obscure the results. Therefore suitable transformations need to be found which transform these measurements into distributions with an approximate Gaussian shape. Typical choices in the biomarker area are transformations of the form log(x+c). These transformations do not change the order of the values, such that non-parametric analyses based on ranks or cut-offs remain unchanged by the transformation. Such transformations are also a prerequisite when linear multivariate approaches like e.g. Discriminant Analysis and Principle Component Analysis are to be used.

The basic statistics and interdependencies of the different markers were descriptively investigated. Methodological analyses comparing different measurement approaches, e.g. for IHC, were performed with regard to reliability and validity. Benefit to Tarceva® is defined by the clinical endpoints survival time (or Time to Death, TTD), PFS time (time to progression, TTP/D), objective response, best response (CR/PRISD/PD).

The p-values emerging from these analyses are not to be interpreted in a confirmative sense; they are to be seen as a special descriptive tool in order to guide the exploration towards an efficient candidate prediction rule. Markers were evaluated on a univariate level regarding their potential for prediction (e.g. search for cut-offs) of the clinical endpoints. Further multivariate techniques (e.g. Linear Discriminant Analysis, Multiple Logistic Regression, Principal Component Analysis with Rotation, Cluster Analysis, CART methodology) were employed in order to study combinations of markers. Biomarker and response correlations with clinical covariates were investigated. Candidate groupings derived from biomarkers were checked with time to event variables (Kaplan-Meier curves, Cox proportional hazard model, logrank test).

Results:

Analysis of the TMA Sample Subset in Comparison to the Overall Study Population

The patient subset with samples for biomarker analysis was compared to the overall study population regarding baseline patient characteristics and clinical outcome parameters. The summary is shown in the table below.

| | Main Clinical Population | | Patient subset with IHC/FISH biomarker data | |
|---|---|---|---|---|
| | Placebo (N = 582) | Tarceva ® (N = 580) | Placebo (N = 70) | Tarceva ® (N = 71) |
| Age (years) | 59.1 | 59.9 | 57.5 | 59.1 |
| Male (%) | 75.3 | 78.6 | 80.0 | 74.6 |
| Disease stage IV (%) | 67.2 | 64.8 | 74.3 | 80.3 |
| Adeno carcinoma (%) | 37.6 | 37.9 | 41.4 | 46.5 |
| # of metastatic sites | 3.7 | 3.7 | 3.4 | 4.0 |
| # of affected organs | 2.5 | 2.5 | 2.1 | 2.4 |
| Sum longest diameter | 92.8 | 95.4 | 80.1 | 93.5 |
| Average symptom burden | 26.5 | 26.7 | 24.3 | 25.3 |
| Responders (%) | 38.3 (N = 418) | 42.4 (N = 396) | 42.3 (N = 52) | 43.5 (N = 46) |
| Hazard ratio TTD | 1.035 | | 1.217 | |
| Hazard ratio TTP | 0.980 | | 1.262 | |

Findings:

The patient subset with biomarker data is not representative for the BO16411 study population. There are differences in hazard ratios for TTD and TTP between main population and the biomarker subgroup. Tarceva®-treated patients of the biomarker subgroup have a worse prognosis compared to the main clinical population. Several baseline covariates indicate that the biomarker subgroup—and within this subgroup particularly Tarceva®-related patients represented a more morbid case mix as compared to the main study population. KM plots (FIGS. 1 to 4) should be taken into account as well.

Results of pMAPK IHC Analysis pMAPK IHC data showed sufficient scatter to be eligible for further statistical analysis.

For determining correlation between pMAPK expression and clincal outcome, cut-off values were established by descriptive statistical analysis: Franklin H-score was determined by combining staining intensity and percentage of stained tumor cells (pMAPK_hsco=(pMAPK_Nuclear_Staining+1)*pMAPK_Nuclear_Pos_Cells; range: 0-400). "Positive" pMAPK staining was defined by H-scores of =/>100, else the staining was "negative". Kaplan-Meier plots are shown in FIGS. 5 to 8

| pMAPK H-Score (Cutpoint 100) - COX Model without covariates | | | | | | | |
|---|---|---|---|---|---|---|---|
| Variable | Estimate | Parameter Error | Standard Chi-Square | Pr > ChiSq | Hazard Ratio | 95% Hazard Ratio Confidence Limits | |
| Time to progression/death | | | | | | | |
| trtgr only | 0.27747 | 0.21560 | 1.6562 | 0.1981 | 1.320 | 0.865 | 2.014 |
| trtgr | 0.12352 | 0.22058 | 0.3136 | 0.5755 | 1.131 | 0.734 | 1.743 |
| pMAPK (≧100) | 0.90942 | 0.23706 | 14.7164 | 0.0001 | 2.483 | 1.560 | 3.951 |
| trtgr pMAPK < 100 | 0.49122 | 0.30087 | 2.6656 | 0.1025 | 1.634 | 0.906 | 2.947 |
| trtgr pMAPK ≧ 100 | −0.25703 | 0.30706 | 0.7007 | 0.4026 | 0.773 | 0.424 | 1.412 |
| Time to death | | | | | | | |
| trtgr only | 0.15228 | 0.27818 | 0.2997 | 0.5841 | 1.164 | 0.675 | 2.009 |
| trtgr | −0.02494 | 0.28668 | 0.0076 | 0.9307 | 0.975 | 0.556 | 1.711 |
| pMAPK (≧100) | 0.73352 | 0.29272 | 6.2797 | 0.0122 | 2.082 | 1.173 | 3.696 |
| trtgr pMAPK < 100 | 0.98292 | 0.45017 | 4.7674 | 0.0290 | 2.672 | 1.106 | 6.457 |
| trtgr pMAPK ≧ 100 | −0.70524 | 0.36205 | 3.7943 | 0.0514 | 0.494 | 0.243 | 1.004 |

Findings:

For patients treated with chemotherapy/placebo "positive" pMAPK expression is associated with worse prognosis (TTD: HR 4.882, p=0.0001), while "negative" pMAPK expression appears to be associated with longer survival Trend: "Positive pMAPK" patients might benefit from the chemotherapy/Tarceva® combo (HR 0.500, p: 0.0516)(----)

Figure 9:
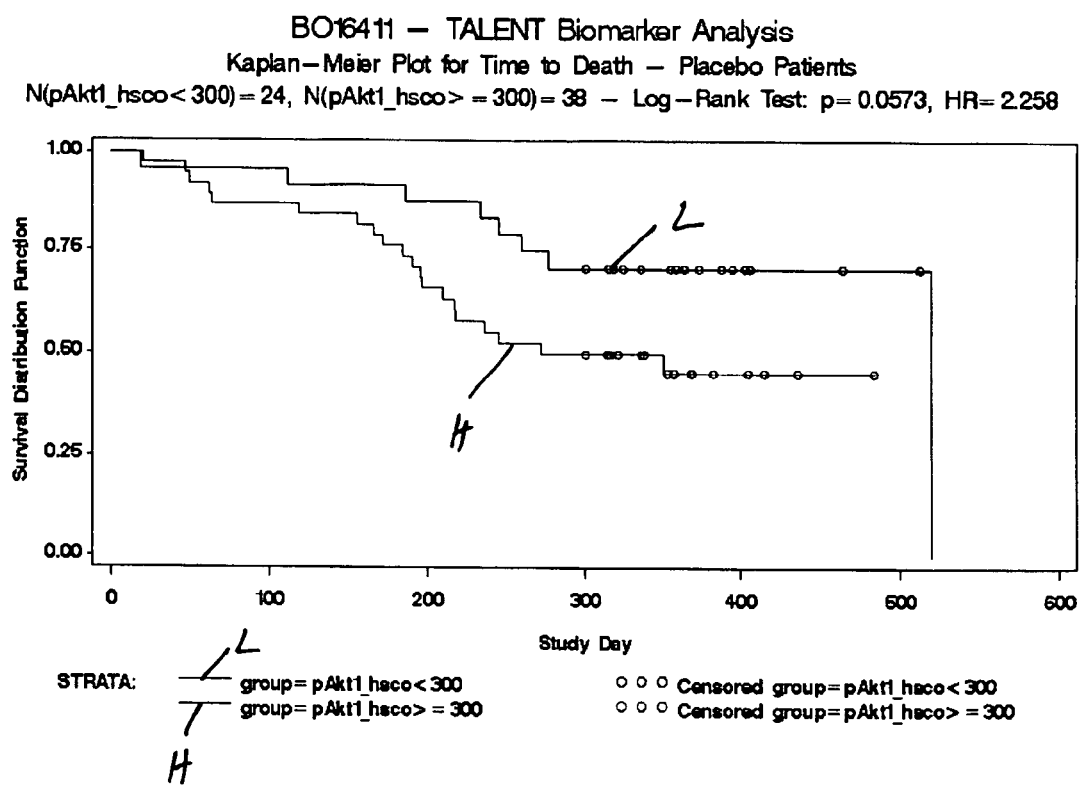
Figure 10:
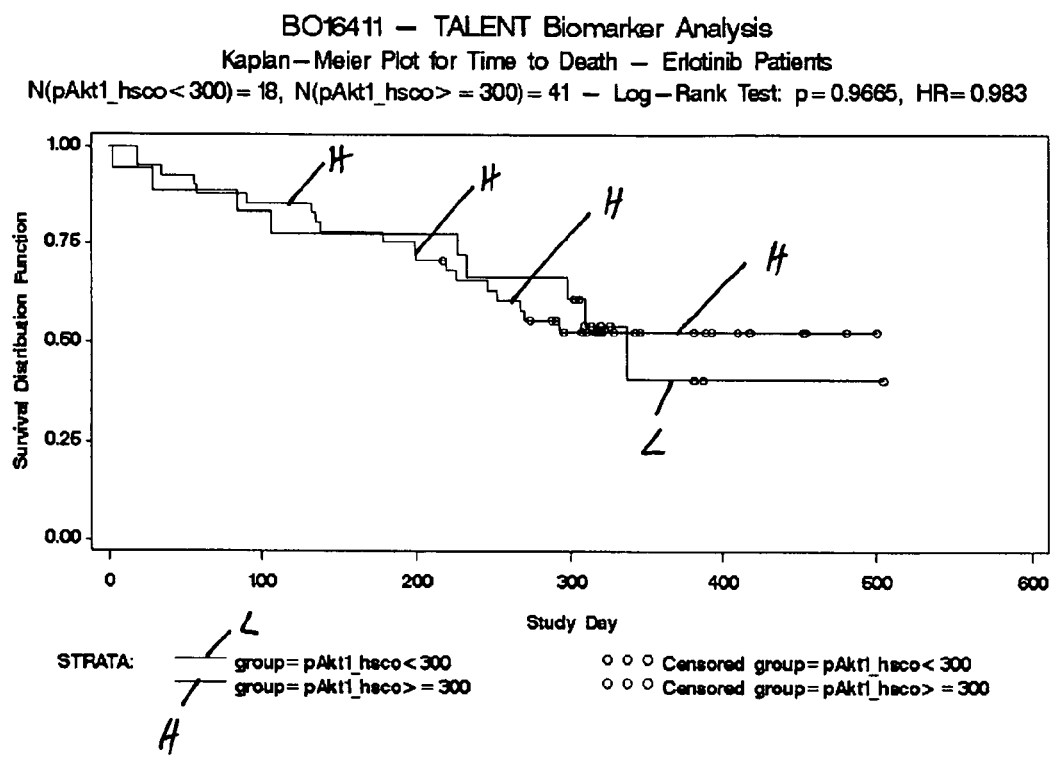
Figure 11:
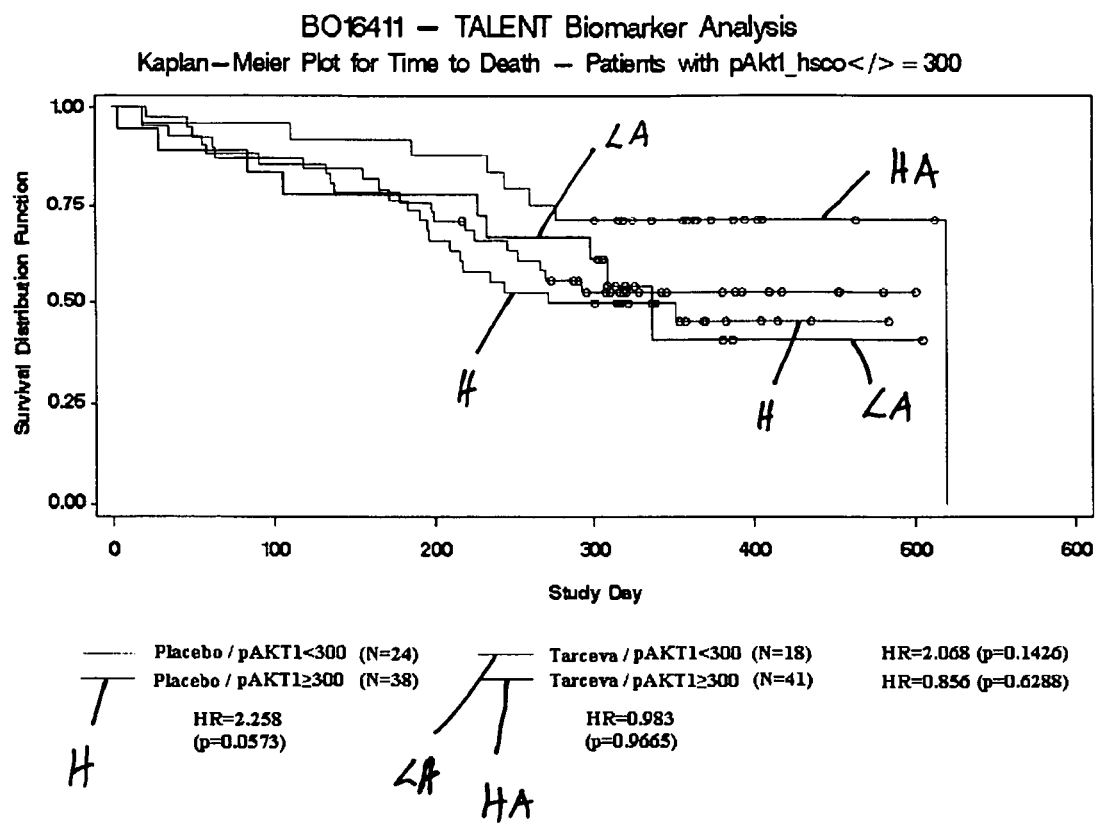

Results of pAKT IHC Analysis pAKT IHC data showed sufficient scatter to be eligible for further statistical analysis For determining correlation between pAKT expression and clincal outcome, cut-off values were established by descriptive statistical analysis: Franklin H-score was determined by combining nuclear staining intensity and percentage of stained tumor cells (pAKT_hsco= (pAKT_Nuclear_Staining+1)*pAKT_Nuclear_Pos_Cells; range: 0-400). "Positive" pAKT staining was defined by H-scores of =/>300, else the staining was "negative". Kaplan-Meier plots are shown in FIGS. 9 to 11

| Correlation of IHC and clinical data | | | | | | | |
|---|---|---|---|---|---|---|---|
| pAKT1 H-Score (Cutpoint 300) - COX Model without covariates | | | | | | | |
| Variable | Estimate | Parameter Error | Standard Chi-Square | Pr > ChiSq | Hazard Ratio | 95% Hazard Ratio Confidence Limits | |
| Time to progression/death | | | | | | | |
| trtgr only | 0.23796 | 0.20820 | 1.3064 | 0.2530 | 1.269 | 0.844 | 1.908 |
| trtgr | 0.19809 | 0.20973 | 0.8921 | 0.3449 | 1.219 | 0.808 | 1.839 |
| pAKT1 (≧300) | 0.66669 | 0.23379 | 8.1320 | 0.0043 | 1.948 | 1.232 | 3.080 |
| trtgr pAKT1 < 300 | 0.12333 | 0.37441 | 0.1085 | 0.7419 | 1.131 | 0.543 | 2.356 |
| trtgr pAKT1 ≧ 300 | 0.23300 | 0.25463 | 0.8373 | 0.3602 | 1.262 | 0.766 | 2.079 |
| Time to death | | | | | | | |
| trtgr only | 0.14794 | 0.27012 | 0.3000 | 0.5839 | 1.159 | 0.683 | 1.969 |
| trtgr | 0.10118 | 0.27209 | 0.1383 | 0.7100 | 1.106 | 0.649 | 1.886 |
| pAKT1 (≧300) | 0.39280 | 0.29959 | 1.7191 | 0.1898 | 1.481 | 0.823 | 2.664 |
| trtgr pAKT1 < 300 | 0.69986 | 0.50449 | 1.9244 | 0.1654 | 2.013 | 0.749 | 5.412 |
| trtgr pAKT1 ≧ 300 | −0.14277 | 0.32063 | 0.1983 | 0.6561 | 0.867 | 0.462 | 1.625 |

Findings:

For patients treated with chemotherapy/placebo "positive" pAKT expression is associated with worse prognosis (TTD HR 2.258, p=0.0573), while "negative" PAKT expression appears to be associated with longer survival A similar difference was not found for patients treated with chemotherapy/Tarceva® combo.

---

The invention claimed is:

1. A method of determining whether a biological sample comprising human lung cancer cells is sensitive to a combination of epidermal growth factor receptor (EGFR) inhibitor erlotinib (N-(3-ethynylphenyl-6,7-bis(2-methoxyethoxy) quinazolin-4-amine) and a chemotherapeutic agent, the method comprising determining the overexpression of a phosphorylated AKT protein and a phosphorylated MAPK protein in the sample, wherein phosphorylated AKT protein (SEQ ID NO:6) is phosphorylated at an amino acid position corresponding to amino acid position 473 of the AKT1 protein and MAPK protein (SEQ ID NO:1) is phosphorylated at amino acid positions corresponding to amino acid positions 202 and 204 of MAPK1,
   wherein the overexpression of phosphorylated AKT protein and phosphorylated MAPK protein in the sample is determined by
   a) determining the level of expression of phosphorylated AKT protein and phosphorylated MAPK protein in the biological sample:
   b) determining the level of expression of phosphorylated AKT protein and phosphorylated MAPK protein in a second sample comprising human lung cancer cells that are not sensitive to a combination of epidermal growth factor receptor inhibitor erlotinib and a chemotherapeutic agent; and
   c) determining the difference of the level of expression of phosphorylated AKT protein and phosphorylated MAPK protein determined in step a) and b) thereby determining the overexpression of phosphorylated AKT protein and phosphorylated MAPK protein;
   whereby the overexpression of the phosphorylated AKT protein and the phosphorylated MAPK protein is an indication that the biological sample comprising human lung cancer cells is sensitive to a combination of epidermal growth factor receptor inhibitor erlotinib and a chemotherapeutic agent.

2. The method of claim 1 whereby the difference of the level of expression of phosphorylated AKT protein and phosphorylated MAPK protein determined in step a) and b) is at least 10%.

3. The method of claim 2 whereby the difference of the level of expression of phosphorylated AKT protein and phosphorylated MAPK protein determined in step a) and b) is at least 25%.

4. The method of claim 1, wherein the sample is a primary lung tumor or a metastasis.

5. The method of claim 1 wherein the chemotherapeutic agent is selected from the group consisting of gemcitabine or cis-platin.

6. The method of claim 1, wherein the overexpression of phosphorylated AKT protein or of phosphorylated MAPK protein is determined using a reagent which specifically binds said_phosphorylated AKT_protein or said phosphorylated MAPK protein.

7. The method of claim 6, wherein the reagent which specifically binds the phosphorylated AKT_protein or phosphorylated MAPK protein is an antibody, antibody derivative, or an antibody fragment.

8. The method of claim 1 wherein the overexpression of phosphorylated AKT protein and phosphorylated MAPK protein in the biological_sample is determined by
   a) immunohistochemically staining the biological_sample,
   b) assigning a grade selected from the numbers 1, 2, 3 and 4 for the level of expression of the phosphorylated AKT protein and the phosphorylated MAPK protein upon visual inspection of the staining of the cells in the biological sample,
   c) determining the percentage of cells with the highest detectable grade in the immunohistochemically stained biological sample,
   d) multiplying the assigned grade with the percentage of cells with the highest detectable grade in the immunohistochemically stained biological sample and with the number 100, and
   e) determining overexpression of phosphorylated AKT protein and phosphorylated MAPK protein in the biological sample when the result of the multiplication in step d) is above 100.

9. A method of determining whether a biological sample comprising human lung cancer cells is sensitive to a combination of epidermal growth factor receptor (EGFR) inhibitor erlotinib (N-(3-ethynylphenyl-6,7-bis(2-methoxyethoxy) quinazolin-4-amine) and a chemotherapeutic agent, the method comprising determining the overexpression of a phosphorylated MAPK protein in the sample, wherein MAPK protein (SEQ ID NO:1) is phosphorylated at amino acid positions corresponding to amino acid positions 202 and 204 of MAPK1
   wherein the overexpression of phosphorylated MAPK protein in the sample is determined by
   a) determining the level of expression of phosphorylated MAPK protein in the biological sample:
   b) determining the level of expression of phosphorylated MAPK protein in a second sample comprising human lung cancer cells that are not sensitive to a combination of epidermal growth factor receptor inhibitor erlotinib and a chemotherapeutic agent; and
   c) determining the difference of the level of expression of phosphorylated MAPK protein determined in step a) and b) thereby determining the overexpression of phosphorylated MAPK protein;
   whereby the overexpression of the phosphorylated MAPK protein is an indication that the biological sample comprising human lung cancer cells is sensitive to a combination of epidermal growth factor receptor inhibitor erlotinib and a chemotherapeutic agent.

* * * * *

UNITED STATES PATENT AND TRADEMARK OFFICE
CERTIFICATE OF CORRECTION

PATENT NO. : 7,655,414 B2 Page 1 of 1
APPLICATION NO. : 11/431241
DATED : February 2, 2010
INVENTOR(S) : Brennscheidt et al.

It is certified that error appears in the above-identified patent and that said Letters Patent is hereby corrected as shown below:

Col. 39, Claim 6, line 54 delete "said_phosphorylated AKT_protein or said phorphorylated" and insert -- said phosphorylated AKT protein or said phosphorylated, --

Col. 40, Claim 7, line 2 delete "AKT_protein" and insert -- AKT protein --

Col. 40, Claim 8, line 7 delete "biological_sample" and insert -- biological sample --
      Line 8 delete "biological_" and insert -- biological --

Signed and Sealed this

Sixth Day of April, 2010

David J. Kappos
*Director of the United States Patent and Trademark Office*

SEQUENCE LISTING

<160> NUMBER OF SEQ ID NOS: 8

<210> SEQ ID NO 1
<211> LENGTH: 360
<212> TYPE: PRT
<213> ORGANISM: Homo sapiens

<400> SEQUENCE: 1

```
Met Ala Ala Ala Ala Ala Gly Ala Gly Pro Glu Met Val Arg Gly
 1               5                  10                  15

Gln Val Phe Asp Val Gly Pro Arg Tyr Thr Asn Leu Ser Tyr Ile Gly
                20                  25                  30

Glu Gly Ala Tyr Gly Met Val Cys Ser Ala Tyr Asp Asn Val Asn Lys
                35                  40                  45

Val Arg Val Ala Ile Lys Lys Ile Ser Pro Phe Glu His Gln Thr Tyr
50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
                100                 105                 110

Tyr Lys Leu Leu Lys Thr Gln His Leu Ser Asn Asp His Ile Cys Tyr
                115                 120                 125

Phe Leu Tyr Gln Ile Leu Arg Gly Leu Lys Tyr Ile His Ser Ala Asn
                130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
                180                 185                 190

Tyr Arg Ala Pro Glu Ile Met Leu Asn Ser Lys Gly Tyr Thr Lys Ser
                195                 200                 205

Ile Asp Ile Trp Ser Val Gly Cys Ile Leu Ala Glu Met Leu Ser Asn
                210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
                260                 265                 270

Val Pro Trp Asn Arg Leu Phe Pro Asn Ala Asp Ser Lys Ala Leu Asp
                275                 280                 285

Leu Leu Asp Lys Met Leu Thr Phe Asn Pro His Lys Arg Ile Glu Val
                290                 295                 300

Glu Gln Ala Leu Ala His Pro Tyr Leu Glu Gln Tyr Tyr Asp Pro Ser
305                 310                 315                 320
```

```
Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360

<210> SEQ ID NO 2
<211> LENGTH: 379
<212> TYPE: PRT
<213> ORGANISM: Homo sapiens

<400> SEQUENCE: 2

Met Ala Ala Ala Ala Gln Gly Gly Gly Gly Glu Pro Arg Arg
  1               5                  10                  15

Thr Glu Gly Val Gly Pro Gly Val Pro Gly Glu Val Glu Met Val Lys
                 20                  25                  30

Gly Gln Pro Phe Asp Val Gly Pro Arg Tyr Thr Gln Leu Gln Tyr Ile
             35                  40                  45

Gly Glu Gly Ala Tyr Gly Met Val Ser Ser Ala Tyr Asp His Val Arg
         50                  55                  60

Lys Thr Arg Val Ala Ile Lys Lys Ile Ser Pro Phe Glu His Gln Thr
 65                  70                  75                  80

Tyr Cys Gln Arg Thr Leu Arg Glu Ile Gln Ile Leu Leu Arg Phe Arg
                 85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335
```

```
Thr Asp Glu Pro Val Ala Glu Glu Pro Phe Thr Phe Ala Met Glu Leu
        340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
        370                 375

<210> SEQ ID NO 3
<211> LENGTH: 2934
<212> TYPE: DNA
<213> ORGANISM: Homo sapiens

<400> SEQUENCE: 3
gcccctccct ccgcccgccc gccggcccgc ccgtcagtct ggcaggcagg caggcaatcg      60
gtccgagtgg ctgtcggctc ttcagctctc ccgctcggcg tcttccttcc tcctcccggt     120
cagcgtcggc ggctgcaccg gcggcggcgc agtccctgcg ggaggggcga caagagctga     180
gcggcggccg ccgagcgtcg agctcagcgc ggcggaggcg gcggcggccc ggcagccaac     240
atggcggcgg cggcggcggc gggcgcgggc ccggagatgg tccgcgggca ggtgttcgac     300
gtggggccgc gctacaccaa cctctcgtac atcggcgagg gcgcctacgg catggtgtgc     360
tctgcttatg ataatgtcaa caaagttcga gtagctatca agaaaatcag ccccttgag      420 caccagacct actgccagag aaccctgagg gagataaaaa tcttactgcg cttcagacat     480
gagaacatca ttggaatcaa tgacattatt cgagcaccaa ccatcgagca atgaaaagat     540
gtatatatag tacaggacct catggaaaca gatctttaca agctcttgaa gacacaacac     600
ctcagcaatg accatatctg ctattttctc taccagatcc tcagggggtt aaaatatatc     660
cattcagcta acgttctgca ccgtgacctc aagccttcca acctgctgct caacaccacc     720
tgtgatctca gatctgtga cttttggcctg gccgtgttg cagatccaga ccatgatcac     780
acagggttcc tgacagaata tgtggccaca cgttggtaca gggctccaga aattatgttg     840
aattccaagg gctacaccaa gtccattgat atttggtctg taggctgcat tctggcagaa     900
atgctttcta caggcccat ctttccaggg aagcattatc ttgaccagct gaaacacatt     960
ttgggtattc ttggatcccc atcacaagaa gacctgaatt gtataataaa tttaaaagct    1020
aggaactatt tgctttctct tccacacaaa aataaggtgc catggaacag gctgttccca    1080
aatgctgact ccaaagctct ggacttattg gacaaaatgt tgacattcaa cccacacaag    1140
aggattgaag tagaacaggc tctggcccac ccatatctgg agcagtatta cgacccgagt    1200
gacgagccca tcgccgaagc accattcaag ttcgacatgg aattggatga cttgcctaag    1260
gaaaagctca agaactaat ttttgaagag actgctagat tccagccagg atacagatct    1320
taaatttgtc aggacaaggg ctcagaggac tggacgtgct cagacatcgg tgttcttctt    1380
cccagttctt gaccctggt cctgtctcca gcccgtcttg gcttatccac tttgactcct    1440
ttgagccgtt tggagggggcg gtttctggta gttgtggctt ttatgctttc aaagaatttc    1500
ttcagtccag agaattcctc ctggcagccc tgtgtgtgtc acccattggt gacctgcggc    1560
agtatgtact tcagtgcacc ttactgctta ctgttgcttt agtcactaat tgctttctgg    1620
tttgaaagat gcagtggttc ctcccctctcc tgaatccttt tctacatgat gccctgctga    1680
ccatgcagcc gcaccagaga gagattcttc cccaattggc tctagtcact ggcatctcac    1740
tttatgatag ggaaggctac tacctagggc actttaagtc agtgacagcc ccttatttgc    1800
acttcacctt ttgaccataa ctgttccccc agagcaggag cttgtggaaa taccttggct    1860
```

-continued

```
gatgttgcag cctgcagcaa gtgcttccgt ctccggaatc cttggggagc acttgtccac   1920
gtcttttctc atatcatggt agtcactaac atatataagg tatgtgctat tggcccagct   1980
tttagaaaat gcagtcattt ttctaaataa aaaggaagta ctgcacccag cagtgtcact   2040
ctgtagttac tgtggtcact tgtaccatat agaggtgtaa cacttgtcaa gaagcgttat   2100
gtgcagtact taatgtttgt aagacttaca aaaaagatt taaagtggca gcttcactcg    2160
acatttggtg agagaagtac aaaggttgca gtgctgagct gtgggcggtt tctggggatg   2220
tcccagggtg gaactccaca tgctggtgca tatacgccct tgagctactt caaatgtggt   2280
ttatacctcg cagatacaag aatctttatg aatatacaat tcttttcct tctacagctt    2340
agctccgtct tttcaaccac gaacatttaa aacccgacct actagcactg ttctgtcctc    2400
aagtactcaa atatttctga tactgctgag tcagactgtc agaaaagct agcactaact     2460
cgtgtttgga gctctatcca tatttttactg atctctttaa gtatttgttc ctgccactgt   2520
gtactgtgga gttgactcgg tgttctgtcc cagtgcggtg cctcctcttg acttccccac    2580
tgctctctgt ggtgagaaat ttgccttgtt caataattac tgtaccctcg catgactgtt    2640
acagctttct gtgcagagat gactgtccaa gtgccacatg cctacgattg aaatgaaaac    2700
tctattgtta cctctgagtt gtgttccacg gaaaatgcta ccagcagat catttaggaa     2760
aaataattct attttttagct tttcatttct cagctgtcct ttttttcttgt ttgattttg    2820
acagcaatgg agaatgggtt atataaagac tgcctgctaa tatgaacaga atgcatttg     2880
taattcatga aaataaatgt acatcttcta tcttcaaaaa aaaaaaaaa aaaa            2934
```

<210> SEQ ID NO 4
<211> LENGTH: 1514
<212> TYPE: DNA
<213> ORGANISM: Homo sapiens

<400> SEQUENCE: 4

```
gcccctccct ccgcccgccc gccggcccgc ccgtcagtct ggcaggcagg caggcaatcg     60
gtccgagtgg ctgtcggctc ttcagctctc ccgctcggcg tcttccttcc tcctcccggt    120
cagcgtcggc ggctgcaccg gcggcggcgc agtccctgcg ggaggggcga caagagctga    180
gcggcggccg ccgagcgtcg agctcagcgc ggcggaggcg gcggcggccc ggcagccaac    240
atggcggcgg cggcggcggc gggcgcgggc ccggagatgg tccgcgggca ggtgttcgac    300
gtggggccgc gctacaccaa cctctcgtac atcggcgagg gcgcctacgg catggtgtgc    360
tctgcttatg ataatgtcaa caaagttcga gtagctatca agaaaatcag cccctttgag    420
caccagacct actgccagag aaccctgagg gagataaaaa tcttactgcg cttcagacat    480
gagaacatca ttggaatcaa tgacattatt cgagcaccaa ccatcgagca atgaaagat     540
gtatatatag tacaggacct catggaaaca gatctttaca agctcttgaa gacacaacac    600
ctcagcaatg accatatctg ctattttctc taccagatcc tcagagggtt aaaatatatc    660
cattcagcta acgttctgca ccgtgacctc aagccttcca acctgctgct caacaccacc    720
tgtgatctca agatctgtga ctttggcctg gcccgtgttg cagatccaga ccatgatcac    780
acagggttcc tgacagaata tgtggccaca cgttggtaca gggctccaga aattatgttg    840
aattccaagg gctacaccaa gtccattgat atttggtctg taggctgcat tctggcagaa    900
atgcttctca caggcccat ctttccaggg aagcattatc ttgaccagct gaaccacatt     960
ttgggtatc ttggatcccc atcacaagaa gacctgaatt gtataataaa tttaaaagct    1020
```

```
aggaactatt tgctttctct tccacacaaa ataaggtgc catggaacag gctgttccca      1080
aatgctgact ccaaagctct ggacttattg gacaaaatgt tgacattcaa cccacacaag      1140
aggattgaag tagaacaggc tctggcccac ccatatctgg agcagtatta cgacccgagt      1200
gacgagccca tcgccgaagc accattcaag ttcgacatgg aattggatga cttgcctaag      1260
gaaaagctca agaactaat ttttgaagag actgctagat tccagccagg atacagatct       1320
taaatttgtc aggtacctgg agtttaatac agtgagctc agcaagggag gcgctgcctt        1380
ttgtttctag aatattatgt tcctcaaggt ccattatttt gtattctttt ccaagctcct      1440
tattggaagg tattttttta aatttagaat taaaaattat ttagaaaaaa aaaaaaaaaa       1500
aaaaaaaaaa aaaa                                                        1514

<210> SEQ ID NO 5
<211> LENGTH: 1866
<212> TYPE: DNA
<213> ORGANISM: Homo sapiens

<400> SEQUENCE: 5
cgttcctcgg cgccgccggg gccccagagg gcagcggcag caacagcagc agcagcagca        60
gcgggagtgg agatggcggc ggcggcggct caggggggcg ggggcgggga gccccgtaga       120
accgaggggg tcgcccgggg ggtcccgggg gaggtgagaa tggtgaaggg gcagccgttc       180 gacgtggggcc cgcgctacac gcagttgcag tacatcggcg agggcgcgta cggcatggtc       240
agctcggcct atgaccacgt gcgcaagact cgcgtggcca tcaagaagat cagcccctt c      300 gaacatcaga cctactgcca gcgcacgctc cgggagatcc agatcctgct gcgcttccgc       360
catgagaatg tcatcggcat ccgagacatt ctgcgggcgt ccaccctgga agccatgaga       420
gatgtctaca ttgtgcagga cctgatggag actgacctgt acaagttgct gaaaagccag       480
cagctgagca atgaccatat ctgctacttc ctctaccaga tcctgcgggg cctcaagtac       540
atccactccg ccaacgtgct ccaccgagat ctaaagccct caacctgct cagcaacacc        600 acctgcgacc ttaagatttg tgatttcggc ctggcccgga ttgccgatcc tgagcatgac       660
cacaccggct tcctgacgga gtatgtggct acgcgctggt accgggcccc agagatcatg       720
ctgaactcca agggctatac caagtccatc gacatctggt ctgtgggctg cattctggct       780
gagatgctct ctaaccggcc catcttccct ggcaagcact acctggatca gctcaaccac       840
attctgggca tcctgggctc cccatcccag gaggacctga attgtatcat caacatgaag       900
gcccgaaact acctacagtc tctgccctcc aagaccaagg tggcttgggc caagcttttc       960
cccaagtcag actccaaagc ccttgacctg ctggaccgga tgttaacctt taaccccaat      1020
aaacggatca cagtggagga agcgctggct caccctacc tggagcagta ctatgacccg       1080
acggatgagc cagtggccga ggagccttc accttcgcca tggagctgga tgacctacct       1140
aaggagcggc tgaaggagct catcttccag gagacagcac gcttccagcc cggagtgctg      1200
gaggccccct agcccagaca gacatctctg caccctgggg cctggacctg cctcctgcct      1260 gccctctcc cgccagactg ttagaaaatg gacactgtgc ccagcccgga ccttggcagc      1320
ccaggccggg gtggagcatg ggcctggcca cctctctcct ttgctgaggc ctccagcttc      1380
aggcaggcca aggccttctc ctccccaccc gccctcccca cggggcctcg ggagctcagg      1440
tggccccagt tcaatctccc gctgctgctg ctgctgcgcc cttaccttcc ccagcgtccc      1500
agtctctggc agttctggaa tggaagggtt ctggctgccc caacctgctg aagggcagag      1560
gtggagggtg gggggcgctg agtagggact cagggccatg cctgccccc tcatctcatt      1620
```

-continued

```
caaaccccac cctagtttcc ctgaaggaac attccttagt ctcaagggct agcatccctg    1680
aggagccagg ccgggccgaa tcccctccct gtcaaagctg tcacttcgcg tgccctcgct    1740
gcttctgtgt gtggtgagca gaagtggagc tgggggggcgt ggagagcccg gcgcccctgc    1800
cacctccctg acccgtctaa tatataaata tagagatgtg tctatggctg aaaaaaaaaa    1860
aaaaaa                                                                 1866

<210> SEQ ID NO 6
<211> LENGTH: 480
<212> TYPE: PRT
<213> ORGANISM: Homo sapiens

<400> SEQUENCE: 6

Met Ser Asp Val Ala Ile Val Lys Glu Gly Trp Leu His Lys Arg Gly
  1               5                  10                  15

Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
         35                  40                  45

Glu Ala Pro Leu Asn Asn Phe Ser Val Ala Gln Cys Gln Leu Met Lys
     50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320
```

```
Leu Glu Asp Asn Asp Tyr Gly Arg Ala Val Asp Trp Trp Gly Leu Gly
            325                 330                 335

Val Val Met Tyr Glu Met Met Cys Gly Arg Leu Pro Phe Tyr Asn Gln
        340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
        370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
            405                 410                 415

Tyr Glu Lys Lys Leu Ser Pro Pro Phe Lys Pro Gln Val Thr Ser Glu
        420                 425                 430

Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Gly Thr Ala
465                 470                 475                 480

<210> SEQ ID NO 7
<211> LENGTH: 481
<212> TYPE: PRT
<213> ORGANISM: Homo sapiens

<400> SEQUENCE: 7

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
        115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
            180                 185                 190

Glu Val Ala His Thr Val Thr Glu Ser Arg Val Leu Gln Asn Thr Arg
        195                 200                 205

His Pro Phe Leu Thr Ala Leu Lys Tyr Ala Phe Gln Thr His Asp Arg
    210                 215                 220
```

```
Leu Cys Phe Val Met Glu Tyr Ala Asn Gly Gly Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
            260                 265                 270

Tyr Arg Asp Ile Lys Leu Glu Asn Leu Met Leu Asp Lys Asp Gly His
                275                 280                 285

Ile Lys Ile Thr Asp Phe Gly Leu Cys Lys Glu Gly Ile Ser Asp Gly
290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
                355                 360                 365

Phe Pro Arg Thr Leu Ser Pro Glu Ala Lys Ser Leu Leu Ala Gly Leu
370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
            420                 425                 430

Glu Val Asp Thr Arg Tyr Phe Asp Asp Glu Phe Thr Ala Gln Ser Ile
                435                 440                 445

Thr Ile Thr Pro Pro Asp Arg Tyr Asp Ser Leu Gly Leu Leu Glu Leu
450                 455                 460

Asp Gln Arg Thr His Phe Pro Gln Phe Ser Tyr Ser Ala Ser Ile Arg
465                 470                 475                 480

Glu

<210> SEQ ID NO 8
<211> LENGTH: 479
<212> TYPE: PRT
<213> ORGANISM: Homo sapiens

<400> SEQUENCE: 8

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
                20                  25                  30

Gly Ser Phe Ile Gly Tyr Lys Glu Lys Pro Gln Asp Val Asp Leu Pro
            35                  40                  45

Tyr Pro Leu Asn Asn Phe Ser Val Ala Lys Cys Gln Leu Met Lys Thr
50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110
```

```
Glu Glu Glu Arg Met Asn Cys Ser Pro Thr Ser Gln Ile Asp Asn Ile
            115                 120                 125

Gly Glu Glu Met Asp Ala Ser Thr Thr His His Lys Arg Lys Thr
130             135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
    290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
    370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
    450                 455                 460

Arg Pro His Phe Pro Gln Phe Ser Tyr Ser Ala Ser Gly Arg Glu
465                 470                 475
```